US011567079B2

(12) United States Patent
Faatz et al.

(10) Patent No.: US 11,567,079 B2
(45) Date of Patent: Jan. 31, 2023

(54) SOLUBLE AND IMMUNOREACTIVE VARIANTS OF HTLV CAPSID ANTIGEN P24

(71) Applicant: Roche Diagnostics Operations, Inc., Indianapolis, IN (US)

(72) Inventors: Elke Faatz, Huglfing (DE); Christian Scholz, Penzberg (DE); Peter Muench, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/577,175

(22) Filed: Sep. 20, 2019

(65) Prior Publication Data

US 2020/0033342 A1 Jan. 30, 2020

Related U.S. Application Data

(60) Division of application No. 15/246,607, filed on Aug. 25, 2016, now Pat. No. 10,466,242, which is a continuation of application No. PCT/EP2015/053966, filed on Feb. 26, 2015.

(30) Foreign Application Priority Data

Feb. 28, 2014 (EP) .................................... 14157165

(51) Int. Cl.
*C07K 14/005* (2006.01)
*C07K 14/15* (2006.01)
*G01N 33/569* (2006.01)

(52) U.S. Cl.
CPC ..... *G01N 33/56988* (2013.01); *C07K 14/005* (2013.01); *C07K 14/15* (2013.01); *G01N 33/56983* (2013.01); *C07K 2319/35* (2013.01); *C12N 2740/14022* (2013.01); *C12N 2740/14031* (2013.01); *C12N 2740/14051* (2013.01); *G01N 2333/15* (2013.01); *G01N 2469/20* (2013.01)

(58) Field of Classification Search
None
See application file for complete search history.

(56) References Cited

U.S. PATENT DOCUMENTS 6,110,662 A 8/2000 Foung et al.

FOREIGN PATENT DOCUMENTS

| CA | 2626423 A1 | 10/2008 |
| CN | 1377276 A | 10/2002 |
| CN | 101289513 A | 10/2008 |
| CN | 101591665 A | 12/2009 |
| EP | 0214555 A1 | 3/1987 |
| EP | 1982993 A2 | 10/2008 |
| EP | 2127678 A1 | 12/2009 |
| JP | 2000-078973 A | 3/2000 |
| WO | 1992001713 A1 | 2/1992 |
| WO | 1996039630 A1 | 12/1996 |
| WO | 1998013496 A1 | 4/1998 |
| WO | 200110457 A2 | 2/2001 |

OTHER PUBLICATIONS

GenBank Accession No. ABC69558 (Sep. 27, 2005) (Year: 2005).*
Manns et al., Int. J. Cancer, 1992, 51:886-891. (Year: 1992).*
Dahiyat, et al., Protein Design: Fully Automated Sequence Selection, Science, 1997, pp. 82-87, vol. 278.
Dahiyat, et al., Protein Design: Towards Fully Automated Sequence Selection, Journal of Molecular Biology, 1997, pp. 789-796, vol. 273.
Khorasanizadeh, et al., Solution Structure of the Capsid Protein From the Human T-cell Leukemia Virus Type-1, Journal of Molecular Biology, 1999, pp. 491-505, vol. 291.
Kuga et al., A gag-env Hybrid Protein of Human T-cell Leukemia Virus Type 1 and its Application to Serum Diagnostics, Japanese Journal of Cancer Research, 1988, pp. 1168-1173, vol. 79.
Manns et al., Detection of Early Human T-Cell Lymphotropic Virus Type 1 Antibody Patterns During Seroconversion Among Transfusion Recipients, Blood, 1991, pp. 896-905, vol. 77, No. 4.
Pace et al., How to measure and predict the molar absorption coefficient of a protein, Protein Science, 1995, pp. 2411-2423, vol. 4.
Porter et al., A thermodynamic definition of protein domains, Proceedings of the National Academy of Sciences USA, 2012, pp. 9120-9125, vol. 109, No. 24.
Scholz et al., Functional Solubilization of Aggregation-prone HIV Envelope Proteins by Covalent Fusion with Chaperone Modules, Journal of Molecular Biology, 2005, pp. 1229-1241, vol. 345.
Struthers, et al., Design of a Monomeric 23-Residue Polypeptide with Defined Tertiary Structure, Science, 1996, pp. 342-345, vol. 271.
Vandamme, et al., Evolutionary strategies of human T-cell lymphotropic virus type II, Gene, 2000, pp. 171-180, vol. 261.
Wang, et al., A novel virus-like particle based on hepatitis B core antigen and substrate-binding domain of bacterial molecular chaperone DnaK Vaccine, 2009, vol. 27, pp. 7377-7384.

* cited by examiner

*Primary Examiner* — Nicole Kinsey White
(74) *Attorney, Agent, or Firm* — Stinson LLP

(57) ABSTRACT

The invention concerns soluble and antigenic HTLV p24 variants that can be fused to chaperones and their use in diagnostic applications such as immunoassays for detecting antibodies against HTLV-I or HTLV-II in an isolated biological sample. In particular, the invention relates to a soluble HTLV-I or HTLV-II p24 antigen comprising either the N- or the C-terminal domain of p24 and lacking the other domain. Moreover, the invention covers recombinant DNA molecules encoding these HTLV-I and -II fusion antigens as well as their recombinant production using expression vectors and host cells transformed with such expression vectors. In addition, the invention focuses on compositions of these HTLV p24 antigens with HTLV gp21 antigen and on an immunoassay method for detection of HTLV antibodies using the antigens of the invention. Also the use of HTLV p24 antigens in an in vitro diagnostic assay as well as a reagent kit for detection of anti-HTLV-antibodies comprising said HTLV antigens is encompassed.

Figure 1:
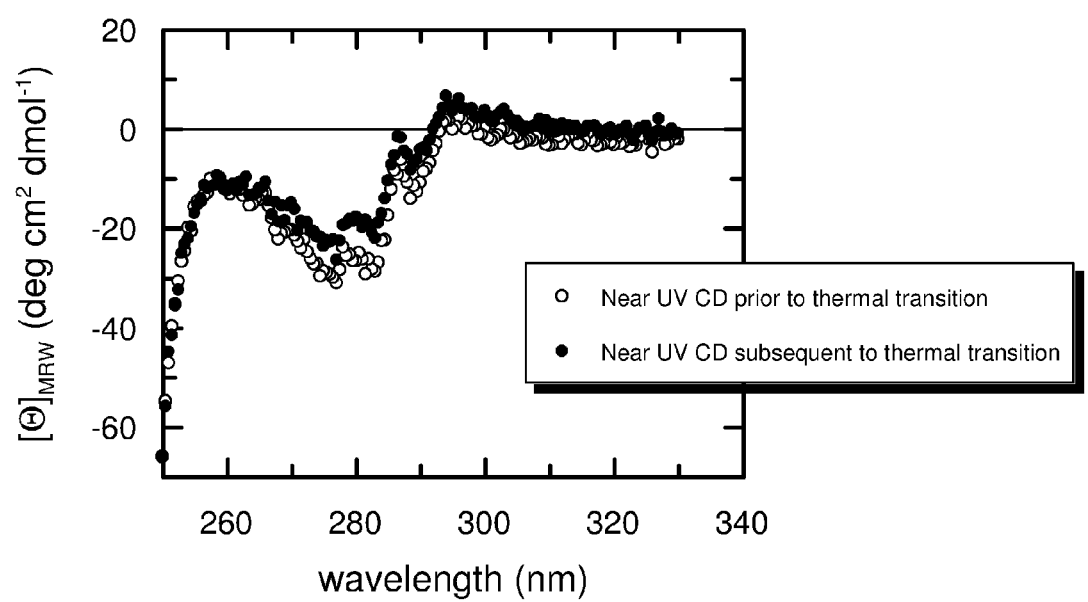

9 Claims, 4 Drawing Sheets
Specification includes a Sequence Listing.

SOLUBLE AND IMMUNOREACTIVE VARIANTS OF HTLV CAPSID ANTIGEN P24

CROSS-REFERENCE TO RELATED APPLICATIONS

This application is a divisional of U.S. application Ser. No. 15/246,607 filed Aug. 25, 2016 (patented as U.S. Pat. No. 10,466,242 on Nov. 5, 2019), which is a continuation of International Patent Application No. PCT/EP2015/053966 filed Feb. 26, 2015, which claims priority to European Patent Application No. 14157165.3 filed Feb. 28, 2014, the disclosures of which are hereby incorporated by reference in their entirety.

INCORPORATION OF SEQUENCE LISTING

A Sequence Listing is provided herein and is herein incorporated by reference. This Sequence Listing consists of SEQ ID NOs:1-27.

BACKGROUND OF THE INVENTION

Human T-cell lymphotropic virus (HTLV) type I (HTLV-I) was the first retrovirus to be discovered in man in 1980. It is the causative agent of T-cell leukemia and/or lymphoma and of HTLV-associated myelopathy, a severe demyelinating condition that eventually leads to tropical spastic paraparesis. The cumulative lifetime risk of developing these fatal and incurable diseases amounts to ~5% in asymptomatic carriers of HTLV-I. HTLV-I infects primarily CD4-positive T-cells. It is also called the adult T-cell lymphoma virus type 1. HTLV-II shares approximately 70% genetic homology (translating into 80-95% structural similarity at the protein level) with HTLV-I. The pathogenic potential of HTLV-II is not yet completely elucidated but HTLV-II is regarded as a risk marker for blood transfusion since it is mainly found in intravenous drug users world-wide (Vandamme et al., Evolutionary strategies of human T-cell lymphotropic virus type II, Gene 261 (2000) 171-180). Both viruses are spread globally, but the prevalence of HTLV-I is highest in hot spot regions in Southern Japan (Kyushu, Shikoku and Okinawa), Sub-Saharan Africa, the Caribbean (Jamaica and Haiti) and South America.

The major transmission modes of HTLV-I/II are through sexual contact, blood transfusion, sharing injection needles and mother to child transmission through breast-feeding. The seroconversion period after HTLV infection is long when compared to other infectious diseases. The window period, i.e. the time frame after infection within which no antibodies against the virus can be detected may range from several weeks to months.

Blood donor screening for HTLV was introduced first in Japan in 1986, in the United States and Canada in 1988/1989, in France in 1991 and in several European and South American countries after 1991. So far no gold standard has emerged for the diagnosis of HTLV infection. Several immunoassays based on recombinant and/or synthetic peptide antigens have been introduced in the past years.

Commercially available immunoassays for detecting anti-HTLV-antibodies often use polypeptides derived from the envelope of the virus (gp46 surface protein and gp21 transmembrane protein) or from the gag-encoded p24 capsid protein.

Due to the long seroconversion time it is important to detect even very small amounts of antibodies once they appear at an early stage after infection. Therefore, the development of appropriate antigens for a highly sensitive immunoassay is mandatory. As a matter of course, it is desirable to close the diagnostic gap between infection and detection, in order to prevent inadvertent spread and propagation of the virus.

It has been known for some time that, upon HTLV-infection, antibodies to the gag proteins appear early in seroconversion. In particular, the gag-encoded capsid antigen p24 is a preferred early target of the humoral immune response (Manns et al., Blood (1991) 77: 896-905). Hitherto, peptidic and recombinant variants of the p24 capsid protein have been used as antigens in immunoassays. By means of these antigens, anti-p24 immunoglobulins of the G-type have been detected with high accuracy and satisfying sensitivity. p24 capsid antigens of this kind are, however, not able to bind and detect immunoglobulins of the M type. Since IgM molecules usually appear before IgG molecules during seroconversion, we reasoned that it should be worthwhile to modify recombinant p24 capsid antigen in a way that it is recognized and bound by IgM. In brief, we wondered whether it was possible to improve the sensitivity of anti-p24 immunoglobulin detection by tailoring and engineering the p24 capsid antigen. In particular, we were seeking to design a p24 variant which was able to interact with and detect IgM molecules.

The problem underlying the invention therefore is the development of an immunoassay for detecting antibodies against HTLV-I and HTLV-II that overcomes the limited seroconversion sensitivity of the hitherto available immunoassays.

The problem is solved by the current invention as specified in the claims.

SUMMARY OF THE INVENTION

The invention concerns soluble HTLV p24 antigens that are fused to chaperones and their use in diagnostic applications such as immunoassays for detecting antibodies against HTLV-I or HTLV-II in an isolated biological sample. In particular, the invention relates to soluble HTLV-I or HTLV-II p24 antigen fragments comprising either the N- or the C-terminal domain of the p24 sequence wherein the HTLV p24 antigen fragment may be fused to a chaperone. Moreover, the invention covers recombinant DNA molecules encoding these HTLV-I and -II fusion antigens as well as their recombinant production using expression vectors and host cells transformed with such expression vectors. In addition, the invention focusses on compositions of several of these HTLV p24 antigens and on an immunoassay method for detection of HTLV antibodies using the antigens of the invention. Also the use of HTLV p24 antigens in an in vitro diagnostic assay as well as a reagent kit for detection of anti-HTLV-antibodies comprising said HTLV p24 antigens is encompassed.

Legend to the Disclosed Amino Acid Sequences

SEQ ID NO. 1: p24/HTLV-I (146-344)// P10274, 199 amino acid residues

Shows the HTLV-I p24 sequence as retrieved from SwissProt database ID P10274 (146-344 Gag-Pro polyprotein from Human T-cell leukemia virus 1, strain Japan ATK-1 subtype A). The numbering refers to the immature polyprotein precursor (sequence of aa 1-130 refers to matrix protein p19). Note that the N-terminal 15 amino acid residues from aa 131-145 (proline rich sequence) have been omitted.

```
SEQ ID NO. 2: p24 NTD (146-260)/HTLV-I,
115 amino acid residues
QMKDLQAIKQ EVSQAAPGSP QFMQTIRLAV QQFDPTAKDL

QDLLQYLCSS LVASLHHQQL DSLISEAETR GITGYNPLAG

PLRVQANNPQ QQGLRREYQQ LWLAAFAALP GSAKDPSWAS

ILQGLEEPYH AFVERLNIAL DNGLPEGTPK DPILRSLAYS

NANKECQKLL QARGHTNSPL GDMLRACQTW TPKDKTKVL
```

Shows the N-terminal domain of HTLV-I p24 from amino acid 146-260 (for numbering of amino acid positions see also SEQ ID NO. 1). Note that one position is marked as X (underlined) which means that the cysteine residue of the natural sequence may be replaced by an alanine or serine (X=C, A or S).

```
SEQ ID NO. 3: p24 CTD (261-344)/HTLV-I,
84 amino acid residues
QMKDLQAIKQ EVSQAAPGSP QFMQTIRLAV QQFDPTAKDL

QDLLQYLXSS LVASLHHQQL DSLISEAETR GITGYNPLAG

PLRVQANNPQ QQGLRREYQQ LWLAAFAALP GSAKD
```

Shows the C-terminal domain of HTLV-I p24 from amino acid residues 261-344 (for numbering of amino acid positions see also SEQ ID NO. 1). Note that two positions are marked as X (underlined) which means that the cysteine residues of the natural sequence may be replaced by alanine or serine (X=C, A or S).

```
SEQ ID NO. 4: p24 (146-344)/HTLV-I,
199 amino acid residues
PSWASILQGL EEPYHAFVER LNIALDNGLP EGTPKDPILR

SLAYSNANKE XQKLLQARGH TNSPLGDMLR AXQTWTPKDK

TKVL
```

Shows the HTLV-I p24 sequence similar to SEQ ID NO. 1 with regard to length and position. However, three amino acid positions show an X (underlined) which means that in these positions the naturally occurring cysteines (positions no. 193, 311 and 332 numbered according to the precursor polypeptide sequence) may be substituted by alanine or serine (X=C, A or S).

```
SEQ ID NO. 5: p24/HTLV-II (152-350)//P03353,
199 amino acid residues
QMKDLQAIKQ EVSQAAPGSP QFMQTIRLAV QQFDPTAKDL

QDLLQYLXSS LVASLHHQQL DSLISEAETR GITGYNPLAG

PLRVQANNPQ QQGLRREYQQ LWLAAFAALP GSAKDPSWAS

ILQGLEEPYH AFVERLNIAL DNGLPEGTPK DPILRSLAYS

NANKEXQKLL QARGHTNSPL GDMLRAXQTW TPKDKTKVL
```

Shows the HTLV-II p24 sequence as retrieved from SwissProt database ID P03353 (152-3350 Gag-Pro polyprotein from Human T-cell leukemia virus 2). The numbering refers to the immature polyprotein precursor (sequence of aa 1-136 refers to matrix protein p19). Note that the N-terminal 15 amino acids from aa 137-151 (proline rich sequence) have been omitted.

```
SEQ ID NO. 6: p24 NTD (152-266)/HTLV-II,
115 amino acid residues
QMKDLQAIKQ EVSSSALGSP QFMQTLRLAV QQFDPTAKDL

QDLLQYLCSS LVVSLHHQQL NTLITEAETR GMTGYNPMAG

PLRMQANNPA QQGLRREYQN LWLAAFSTLP GNTRDPSWAA

ILQGLEEPYC AFVERLNVAL DNGLPEGTPK EPILRSLAYS

NANKECQKIL QARGHTNSPL GEMLRTCQAW TPKDKTKVL
```

Shows the N-terminal domain of HTLV-II p24 from amino acid 152-266 (for numbering of amino acid positions see also SEQ ID NO. 5). Note that one position is marked as X (underlined) which means that the cysteine residue of the natural sequence may be replaced by an alanine or serine (X=C, A or S).

```
SEQ ID NO. 7: p24 CTD (267-350)/HTLV-II,
84 amino acid residues
QMKDLQAIKQ EVSSSALGSP QFMQTLRLAV QQFDPTAKDL

QDLLQYLXSS LVVSLHHQQL NTLITEAETR GMTGYNPMAG

PLRMQANNPA QQGLRREYQN LWLAAFSTLP GNTRD
```

Shows the C-terminal domain of HTLV-II p24 from amino acid 267-350 (for numbering of amino acid positions see also SEQ ID NO. 5). Note that three positions are marked as X (underlined) which means that the cysteine residues of the natural sequence may be replaced by alanine or serine (X=C, A or S).

```
SEQ ID NO. 8: p24 (152-350)/HTLV-II,
199 amino acid residues
PSWAAILQGL EEPYXAFVER LNVALDNGLP EGTPKEPILR

SLAYSNANKE XQKILQARGH TNSPLGEMLR TXQAWTPKDK TKVL
```

Shows the HTLV-II p24 sequence similar to SEQ ID NO. 5 with regard to length and position.

Four amino acid positions show an X (underlined) which means that in these positions the naturally occurring cysteines (positions no. 199, 281, 317 and 338 numbered according to the precursor polypeptide sequence) can be substituted by alanine or serine (X=C, A or S).

```
QMKDLQAIKQ EVSSSALGSP QFMQTLRLAV QQFDPTAKDL

QDLLQYLXSS LVVSLHHQQL NTLITEAETR GMTGYNPMAG

PLRMQANNPA QQGLRREYQN LWLAAFSTLP GNTRDPSWAA

ILQGLEEPYX AFVERLNVAL DNGLPEGTPK EPILRSLAYS

NANKEXQKIL QARGHTNSPL GEMLRTXQAW TPKDKTKVL
```

The following amino acid sequences (SEQ ID NOs. 9-16 and 18-24) show fusion sequences of HTLV-I or HTLV-II p24 (complete or partial) sequences as used in the examples section. The two letters Ec in the protein designations for EcSlyD, EcFkpA and EcSkp indicate the protein sequence origin from *Escherichia coli*. Each protein bears a hexa-histidine tag at its C-terminal end which is used to facilitate protein purification and refolding.

SEQ ID NO. 9: EcSlyD-EcSlyD-p24(146-344)/
HTLV-I
MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGVVH GAHDHHHDHD HDGGGSGGGS
GGGSGGGSGG GSGGGQMKDL QAIKQEVSQA APGSPQFMQT
IRLAVQQFDP TAKDLQDLLQ YLASSLVASL HHQQLDSLIS
EAETRGITGY NPLAGPLRVQ ANNPQQQGLR REYQQLWLAA
FAALPGSAKD PSWASILQGL EEPYHAFVER LNIALDNGLP
EGTPKDPILR SLAYSNANKE AQKLLQARGH TNSPLGDMLR
AAQTWTPKDK TKVLLEHHHH HH

SEQ ID NO. 10: EcFkpA-p24(146-344)/
HTLV-I
MAEAAKPATT ADSKAAFKND DQKSAYALGA SLGRYMENSL
KEQEKLGIKL DKDQLIAGVQ DAFADKSKLS DQEIEQTLQA
FEARVKSSAQ AKMEKDAADN EAKGKEYREK FAKEKGVKTS
STGLVYQVVE AGKGEAPKDS DTVVVNYKGT LIDGKEFDNS
YTRGEPLSFR LDGVIPGWTE GLKNIKKGGK IKLVIPPELA
YGKAGVPGIP PNSTLVFDVE LLDVKPAPKA DAKPEADAKA
ADSAKKGGGS GGGSGGGSGG GSGGGSGGGQ MKDLQAIKQE
VSQAAPGSPQ FMQTIRLAVQ QFDPTAKDLQ DLLQYLASSL
VASLHHQQLD SLISEAETRG ITGYNPLAGP LRVQANNPQQ
QGLRREYQQL WLAAFAALPG SAKDPSWASI LQGLEEPYHA
FVERLNIALD NGLPEGTPKD PILRSLAYSN ANKEAQKLLQ
ARGHTNSPLG DMLRAAQTWT PKDKTKVLLE HHHHHH

SEQ ID NO. 11: EcSlyD-EcSlyD-p24/
CTD(258-344)/HTLV-I
MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGHVH GAHDHHHDHD HDGGGSGGGS
GGGSGGGSGG GSGGGAKDPS WASILQGLEE PYHAFVERLN

-continued

IALDNGLPEG TPKDPILRSL AYSNANKEAQ KLLQARGHTN
SPLGDMLRAA QTWTPKDKTK VLEHHHHHH

SEQ ID NO. 12: EcFkpA-p24/CTD(258-344)/
HTLV-I
MAEAAKPATT ADSKAAFKND DQKSAYALGA SLGRYMENSL
KEQEKLGIKL DKDQLIAGVQ DAFADKSKLS DQEIEQTLQA
FEARVKSSAQ AKMEKDAADN EAKGKEYREK FAKEKGVKTS
STGLVYQVVE AGKGEAPKDS DTVVVNYKGT LIDGKEFDNS
YTRGEPLSFR LDGVIPGWTE GLKNIKKGGK IKLVIPPELA
YGKAGVPGIP PNSTLVFDVE LLDVKPAPKA DAKPEADAKA
ADSAKKGGGS GGGSGGGSGG GSGGGSGGGA KDPSWASILQ
GLEEPYHAFV ERLNIALDNG LPEGTPKDPI LRSLAYSNAN
KEAQKLLQAR GHTNSPLGDM LRAAQTWTPK DKTKVLEHHH
HHH

SEQ ID NO. 13: EcSkp-p24/CTD(258-344)/HTLV-I
MADKIAIVNM GSLFQQVAQK TGVSNTLENE FRGRASELQR
METDLQAKMK KLQSMKAGSD RTKLEKDVMA QRQTFAQKAQ
AFEQDRARRS NEERGKLVTR IQTAVKSVAN SQDIDLVVDA
NAVAYNSSDV KDITADVLKQ VKGGGSGGGS GGGSGGGSGG
GSGGGAKDPS WASILQGLEE PYHAFVERLN IALDNGLPEG
TPKDPILRSL AYSNANKEAQ KLLQARGHTN SPLGDMLRAA
QTWTPKDKTK VLEHHHHHH

SEQ ID NO. 14: EcSlyD-EcSlyD-p24/
NTD(146-260)/HTLV-I
MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGHVH GAHDHHHDHD HDGGGSGGGS
GGGSGGGSGG GSGGGQMKDL QAIKQEVSQA APGSPQFMQT
IRLAVQQFDP TAKDLQDLLQ YLASSLVASL HHQQLDSLIS
EAETRGITGY NPLAGPLRVQ ANNPQQQGLR REYQQLWLAA
FAALPGSAKD LEHHHHHH

SEQ ID NO. 15: EcFkpA-p24/NTD(146-260)/
HTLV-I
MAEAAKPATT ADSKAAFKND DQKSAYALGA SLGRYMENSL
KEQEKLGIKL DKDQLIAGVQ DAFADKSKLS DQEIEQTLQA
FEARVKSSAQ AKMEKDAADN EAKGKEYREK FAKEKGVKTS
STGLVYQVVE AGKGEAPKDS DTVVVNYKGT LIDGKEFDNS
YTRGEPLSFR LDGVIPGWTE GLKNIKKGGK IKLVIPPELA

-continued

YGKAGVPGIP PNSTLVFDVE LLDVKPAPKA DAKPEADAKA

ADSAKKGGGS GGGSGGGSGG GSGGGSGGGQ MKDLQAIKQE

VSQAAPGSPQ FMQTIRLAVQ QFDPTAKDLQ DLLQYLASSL

VASLHHQQLD SLISEAETRG ITGYNPLAGP LRVQANNPQQ

QGLRREYQQL WLAAFAALPG SAKDLEHHHH HH

SEQ ID NO. 16: EcSkp-p24/NTD(146-260)/
HTLV-I
MADKIAIVNM GSLFQQVAQK TGVSNTLENE FRGRASELQR

METDLQAKMK KLQSMKAGSD RTKLEKDVMA QRQTFAQKAQ

AFEQDRARRS NEERGKLVTR IQTAVKSVAN SQDIDLVVDA

NAVAYNSSDV KDITADVLKQ VKGGGSGGGS GGGSGGGSGG

GSGGGQMKDL QAIKQEVSQA APGSPQFMQT IRLAVQQFDP

TAKDLQDLLQ YLASSLVASL HHQQLDSLIS EAETRGITGY

NPLAGPLRVQ ANNPQQGLR REYQQLWLAA FAALPGSAKD

LEHHHHHH

SEQ ID NO. 17: glycine-rich linker between
fused polypeptides (see example 1)
GGGSGGGSGG GSGGGSGGGS GGG SEQ ID NO. 18: EcSlyD-EcSlyD-p24(152-350)/
HTLV-II
MKVAKDLVVS LAYQVRTEDG VLVDESPVSA PLDYLHGHGS

LISGLETALE GHEVGDKFDV AVGANDAYGQ YDENLVQRVP

KDVFMGVDEL QVGMRFLAET DQGPVPVEIT AVEDDHVVVD

GNHMLAGQNL KFNVEVVAIR EATEEELAHG HVHGAHDHHH

DHDHDGGGSG GGSGGGSGGG SGGGSGGGKV AKDLVVSLAY

QVRTEDGVLV DESPVSAPLD YLHGHGSLIS GLETALEGHE

VGDKFDVAVG ANDAYGQYDE NLVQRVPKDV FMGVDELQVG

MRFLAETDQG PVPVEITAVE DDHVVVDGNH MLAGQNLKFN

VEVVAIREAT EEELAHGHVH GAHDHHHDHD HDGGGSGGGS

GGGSGGGSGG GSGGGQMKDL QAIKQEVSSS ALGSPQFMQT

LRLAVQQFDP TAKDLQDLLQ YLASSLVVSL HHQQLNTLIT

EAETRGMTGY NPMAGPLRMQ ANNPAQQGLR REYQNLWLAA

FSTLPGNTRD PSWAAILQGL EEPYAAFVER LNVALDNGLP

EGTPKEPILR SLAYSNANKE AQKILQARGH TNSPLGEMLR

TAQAWTPKDK TKVLLEHHHH HH

SEQ ID NO. 19: EcFkpA-p24(152-350)/
HTLV-II
MAEAAKPATT ADSKAAFKND DQKSAYALGA SLGRYMENSL

KEQEKLGIKL DKDQLIAGVQ DAFADKSKLS DQEIEQTLQA

FEARVKSSAQ AKMEKDAADN EAKGKEYREK FAKEKGVKTS

STGLVYQVVE AGKGEAPKDS DTVVVNYKGT LIDGKEFDNS

YTRGEPLSFR LDGVIPGWTE GLKNIKKGGK IKLVIPPELA

YGKAGVPGIP PNSTLVFDVE LLDVKPAPKA DAKPEADAKA

ADSAKKGGGS GGGSGGGSGG GSGGGSGGGQ MKDLQAIKQE

VSSSALGSPQ FMQTLRLAVQ QFDPTAKDLQ DLLQYLASSL

VVSLHHQQLN TLITEAETRG MTGYNPMAGP LRMQANNPAQ

QGLRREYQNL WLAAFSTLPG NTRDPSWAAI LQGLEEPYAA

FVERLNVALD NGLPEGTPKE PILRSLAYSN ANKEAQKILQ

ARGHTNSPLG EMLRTAQAWT PKDKTKVLLE HHHHHH

SEQ ID NO. 20: EcSkp-p24(152-350)/HTLV-II
MADKIAIVNM GSLFQQVAQK TGVSNTLENE FRGRASELQR

METDLQAKMK KLQSMKAGSD RTKLEKDVMA QRQTFAQKAQ

AFEQDRARRS NEERGKLVTR IQTAVKSVAN SQDIDLVVDA

NAVAYNSSDV KDITADVLKQ VKGGGSGGGS GGGSGGGSGG

GSGGGQMKDL QAIKQEVSSS ALGSPQFMQT LRLAVQQFDP

TAKDLQDLLQ YLASSLVVSL HHQQLNTLIT EAETRGMTGY

NPMAGPLRMQ ANNPAQQGLR REYQNLWLAA FSTLPGNTRD

PSWAAILQGL EEPYAAFVER LNVALDNGLP EGTPKEPILR

SLAYSNANKE AQKILQARGH TNSPLGEMLR TAQAWTPKDK

TKVLLEHHHH HH

SEQ ID NO. 21: EcFkpA-p24/CTD(267-350)/
HTLV-II
MAEAAKPATT ADSKAAFKND DQKSAYALGA SLGRYMENSL

KEQEKLGIKL DKDQLIAGVQ DAFADKSKLS DQEIEQTLQA

FEARVKSSAQ AKMEKDAADN EAKGKEYREK FAKEKGVKTS

STGLVYQVVE AGKGEAPKDS DTVVVNYKGT LIDGKEFDNS

YTRGEPLSFR LDGVIPGWTE GLKNIKKGGK IKLVIPPELA

YGKAGVPGIP PNSTLVFDVE LLDVKPAPKA DAKPEADAKA

ADSAKKGGGS GGGSGGGSGG GSGGGSGGGP SWAAILQGLE

EPYAAFVERL NVALDNGLPE GTPKEPILRS LAYSNANKEA

QKILQARGHT NSPLGEMLRT AQAWTPKDKT KVLLEHHHHH
H

SEQ ID NO. 22: EcSkp-p24/CTD(267-350)/
HTLV-II
MADKIAIVNM GSLFQQVAQK TGVSNTLENE FRGRASELQR

METDLQAKMK KLQSMKAGSD RTKLEKDVMA QRQTFAQKAQ

AFEQDRARRS NEERGKLVTR IQTAVKSVAN SQDIDLVVDA

NAVAYNSSDV KDITADVLKQ VKGGGSGGGS GGGSGGGSGG

GSGGGPSWAA ILQGLEEPYA AFVERLNVAL DNGLPEGTPK

EPILRSLAYS NANKEAQKIL QARGHTNSPL GEMLRTAQAW

TPKDKTKVLL EHHHHHH

SEQ ID NO. 23: EcFkpA-p24/NTD(152-266)/
HTLV-II
MAEAAKPATT ADSKAAFKND DQKSAYALGA SLGRYMENSL

KEQEKLGIKL DKDQLIAGVQ DAFADKSKLS DQEIEQTLQA

FEARVKSSAQ AKMEKDAADN EAKGKEYREK FAKEKGVKTS

STGLVYQVVE AGKGEAPKDS DTVVVNYKGT LIDGKEFDNS

YTRGEPLSFR LDGVIPGWTE GLKNIKKGGK IKLVIPPELA

YGKAGVPGIP PNSTLVFDVE LLDVKPAPKA DAKPEADAKA

-continued

ADSAKKGGGS GGGSGGGSGG GSGGGSGGGQ MKDLQAIKQE

VSSSALGSPQ FMQTLRLAVQ QFDPTAKDLQ DLLQYLASSL

VVSLHHQQLN TLITEAETRG MTGYNPMAGP LRMQANNPAQ

QGLRREYQNL WLAAFSTLPG NTRDLEHHHH HH

SEQ ID NO. 24: EcSkp-p24/NTD(152-266)/
HTLV-II
MADKIAIVNM GSLFQQVAQK TGVSNTLENE FRGRASELQR

METDLQAKMK KLQSMKAGSD RTKLEKDVMA QRQTFAQKAQ

AFEQDRARRS NEERGKLVTR IQTAVKSVAN SQDIDLVVDA

NAVAYNSSDV KDITADVLKQ VKGGGSGGGS GGGSGGGSGG

GSGGGQMKDL QAIKQEVSSS ALGSPQFMQT LRLAVQQFDP

TAKDLQDLLQ YLASSLVVSL HHQQLNTLIT EAETRGMTGY

NPMAGPLRMQ ANNPAQQGLR REYQNLWLAA FSTLPGNTRD

LEHHHHHH

SEQ ID NO. 25: gp21/HTLV-1 (339-446)//
P14075, 108 amino acid residues

Shows amino acid residues no. 339-446 of envelope glycoprotein gp21 (derived from the env polyprotein precursor) according to SwissProt entry ID P14075. The complete polyprotein precursor comprises: surface protein (=glycoprotein 46, gp46) and transmembrane protein (=glycoprotein 21 gp21) of human T-cell leukemia virus I (isolate Caribbean HS-35 subtype A). Note that three residues are marked as X (underlined) which means that the cysteine residue of the natural sequence may be replaced by an alanine or serine (X=C, A or S).

SLASGKSLLH EVDKDISQLT QAIVKNHKNL LKIAQYAAQN

RRGLDLLFWE QGGLXKALQE QXXFLNITNS HVSILQERPP

LENRVLTGWG LNWDLGLSQW AREALQTG

HTLV gp21 may also be advantageously applied as a solubility-enhanced chaperone fusion polypeptide as shown for example in SEQ ID NOs. 26 and 27

SEQ ID NO. 26: EcSlyD-gp21(339-446)/HTLV-1
MKVAKDLVVS LAYQVRTEDG VLVDESPVSA PLDYLHGHGS

LISGLETALE GHEVGDKFDV AVGANDAYGQ YDENLVQRVP

KDVFMGVDEL QVGMRFLAET DQGPVPVEIT AVEDDHVVVD

GNHMLAGQNL KFNVEVVAIR EATEEELAHG HVHGAHDHHH

DHDHDGGGSG GGSGGGSGGG SGGGSGGGSL ASGKSLLHEV

DKDISQLTQA IVKNHKNLLK IAQYAAQNRR GLDLLFWEQG

GLAKALQEQA AFLNITNSHV SILQERPPLE NRVLTGWGLN

WDLGLSQWAR EALQTGLEHH HHHH

SEQ ID NO. 27: EcSlpA-gp21(339-446)/HTLV-1
SESVQSNSA VLVHFTLKLD DGTTAESTRN NGKPALFRLG

DASLSEGLEQ HLLGLKVGDK TTFSLEPDAA FGVPSPDLIQ

YFSRREFMDA GEPEIGAIML FTAMDGSEMP GVIREINGDS

-continued

ITVDFNHPLA GQTVHFDIEV LEIDPALEGG GSGGGSGGGS

GGGSGGGSGG GSLASGKSLL HEVDKDISQL TQAIVKNHKN

LLKIAQYAAQ NRRGLDLLFW EQGGLAKALQ EQAAFLNITN

SHVSILQERP PLENRVLTGW GLNWDLGLSQ WAREALQTGL

EHHHHHH

BRIEF DESCRIPTION OF THE FIGURES

FIG. 1 shows the near UV CD spectrum of Skp-p24/CTD (267-350), SEQ ID NO. 22.

FIG. 2 shows the melting curve of Skp-p24/CTD (SEQ ID NO. 22). Thermally induced unfolding and refolding is monitored by near UV CD spectroscopy at 277 nm.

FIG. 3 shows the near UV CD spectrum of FkpA-p24/CTD (267-350), SEQ ID NO. 21.

FIG. 4 shows that the near UV CD signal of the native FkpA-p24/CTD molecule is fully restored after a thermally induced unfolding/refolding cycle.

DETAILED DESCRIPTION OF THE INVENTION

HTLV p24 is a crucial antigen for the detection of anti-HTLV antibodies. The p24 capsid protein has been known in the art for a long time and has been used in immunoassays for detection of anti-HTLV antibodies (Manns et al., Blood (1991) 77: 896-905). Immunoassays for the detection of both IgG and IgM molecules require a set of antigens that are recognized and bound not only by IgG molecules but also by IgM molecules. IgM molecules typically occur in the early phase of seroconversion upon infection with HTLV. The binding of the polyvalent IgM molecules is critically dependent on a high antigen epitope density. Thus, it is imperative that antigens designed for the specific detection of IgM molecules possess and display such a high epitope density.

A conventional way to generate IgM detection modules with high epitope density would be to polymerize monomeric antigens by means of chemical crosslinking. There is a wealth of homobifunctional and heterobifunctional crosslinkers that may be used with great advantage and that are well known in the art. Yet, there are some severe drawbacks in the chemically induced polymerization of antigens for use as specifiers in serological assays. For instance, the insertion of crosslinker moieties into antigens may compromise antigenicity by interfering with the native-like conformation or by masking crucial epitopes. Furthermore, the introduction of non-natural tertiary contacts may interfere with the reversibility of protein folding/unfolding, and it may, additionally, be the source of interference problems which have to be overcome by anti-interference strategies in the immunoassay mixture.

A more recent technique of generating IgM detection modules is to fuse the antigen of interest to an oligomeric chaperone, thereby conveying high epitope density to the antigen. The advantage of this technology lies in its high reproducibility and in the triple function of the oligomeric chaperone fusion partner: firstly, the chaperone enhances the expression rate of the fusion polypeptide in the host cell, secondly, the chaperone facilitates the refolding process of the target antigen and enhances its overall solubility and, thirdly, it assembles the target antigen reproducibly into an ordered oligomeric structure.

European patent application publication no. EP1982993A2 discloses a method and tools for early detection of true primary infections by pathogens such as human cytomegalovirus using antigens that are fused to oligomeric chaperones. However, this publication is silent with regard to detection of HTLV infection.

Our initial attempts with the full-length version of HTLV p24 had revealed that this protein exhibits high solubility when fused to EcSlyD-EcSlyD or EcFkpA as a chaperone. Its solubility was, however, limited when p24 was fused to the trimeric Skp chaperone. It is self-evident that solubility of all the compounds is a critical feature for heterogeneous immunoassay applications.

Aggregation processes of proteinaceous ingredients in immunoassays usually result in both a loss of signal (due to the loss of epitopes) and a loss of specificity (due to unspecific binding of labeled antigen aggregate to the solid phase). We observed that full length p24 from HTLV—when fused to the oligomeric chaperone EcSkp—shows a tendency to aggregate in physiological buffer at ambient temperature. Thus, the full-length p24 variant was somewhat precluded from simple and straightforward applications in a sensitive IgM immunoassay.

Instead of focusing on the full-length version of p24, we now tried to design truncated, yet conformationally folded fragments of p24. In other words, we sought to use protein domains instead of the full-length p24 protein as the base for antigen development. A protein domain is an autonomously folding entity within a protein structure, that is, a protein domain is not dependent on other parts or regions of the protein in its folding. To date, many natural protein domains have been elucidated, ranging in size from ~40 amino acid residues (WW domain) to more than 300 amino acid residues. It has also been demonstrated that very small, yet stable protein domains may be designed from the scratch: artificial polypeptide sequences with fragment lengths from 23-28 amino acid sequences have been shown to fold cooperatively and to possess the characteristic features of protein domains (Struthers, M. D. et al., Design of a monomeric 23-residue polypeptide with defined tertiary structure, Science (1996) 271 (5247) 342-345; Dahiyat, B. I. & Mayo, S.L., De novo protein design: fully automated sequence selection, Science (1997) 278 (5335) 82-87; Dahiyat, B. I. et al., De novo protein design: towards fully automated protein design, J. Mol. Biol. (1997) 273 (4) 789-796). From theoretical considerations and experimental evidence it is assumed that the minimal length requirement for a protein domain is around 25 amino acid residues (Porter L. L. & Rose, G. D., A thermodynamic definition of protein domains, PNAS (2012) 109 (24), 9420-9425).

In the Journal of Molecular Biology (1999) August 13; 291(2):491-505, Khorasanizadeh et al. present the NMR structure of the capsid protein p24 and reveal the domain topology of this protein. According to this work, p24 from HTLV-I is largely helical and consists of two well-separated domains, i.e. p24 comprises two well-defined autonomous folding units. The N-terminal domain (NTD) harbors the helices 1-7, whereas the C-terminal domain (CTD) comprises the helices 8-12. We wondered whether it was feasible to express the two domains individually in E. coli, and whether we would be able to obtain oligomeric chaperone polypeptide fusions in a soluble and antigenic form.

Khorasanizadeh et al. are silent with regard to antigenic properties (e.g., B-cell epitopes) of p24 and any diagnostic applications of the NMR-characterized HTLV capsid protein. It has been unpredictable from the mere three-dimensional solution structure of the p24 capsid antigen whether its antigenicity resides mainly in the N-terminal domain (NTD) or in the C-terminal domain (CTD) or whether its B-cell epitopes are evenly spread throughout the molecule.

Surprisingly, we were able to express the isolated HTLV p24 domains NTD and CTD in fusion with chaperone modules such as SlyD, FkpA and Skp. As can be seen in the Examples section, all of these constructs could be purified to homogeneity, they were well soluble and we were able to assess them for their antigenicity with anti-HTLV positive human sera in an automated immunoassay analyzer. The results were quite clear-cut: antigenicity was pretty high for both domains and was even slightly higher for the C-Domain (CTD). Strikingly, NTD could be identified as precarious with respect to the blank values, which were significantly increased when compared to the CTD. CTD exhibited excellent signal dynamics in that it generated high signals with positive sera and very low signals with negative sera. This is surprising, since the CTD is presumed to harbor a natural dimerization motif needed for p24 capsid assembly. By virtue of its natural oligomerization behavior, we had reasoned that the CTD would exhibit an aggregation tendency that is significantly higher than the aggregation tendency of the NTD.

When we assessed p24 CTD and NTD with rabbit anti-HTLV seroconversion sera (there are no commercially available human HTLV seroconversion panels, so we had to recur to an artificial rabbit model), we found that the use of chaperone-induced oligomeric p24 variants on both sides of a DAGS assay tremendously enhances the sensitivity of the immunoassay. Seroconversion samples are recognized much better with oligomeric p24 variants than with monomeric p24 variants.

In brief, the C-domains of p24 from HTLV-I and HTLV-II were identified as p24 fragments with high antigenicity and high solubility. When fused to chaperones such as SlyD, FkpA or Skp, p24 CTD remains soluble, stable and is well-suited for the detection of IgM molecules which typically occur in the early phase of seroconversion upon infection with HTLV. Therefore, in particular the oligomeric FkpA and Skp fusion variants of p24 CTD may serve to enhance the sensitivity of HTLV-immunoassays.

We have developed variants of the capsid protein p24 from HTLV that are more soluble and significantly less aggregation-prone than the full-length p24 molecule. Solubility and stability are improved at the expense of antigenicity—nevertheless, the newly developed p24 variants hold promise as antigens in HTLV immunoassays, since they are abundantly overexpressed in E. coli, are easily purified and refolded via immobilized metal chelate chromatography (IMAC), exhibit satisfying stability properties and may be used to reliably detect anti-HTLV antibodies in human sera (presumably in combination with the ectodomain of gp21, another immunodominant protein from HTLV). It is of paramount importance that, e.g., the FkpA-p24/CTD and Skp-p24/CTD fusion proteins form natural oligomers with epitope densities that are sufficient to detect IgM molecules. Since we aimed at developing an immunoassay for total immunoglobulin detection (i.e. detection of IgG and IgM), the oligomeric species FkpA-p24/CTD and Skp-p24/CTD may be used advantageously as specifiers on both sides of a DAGS format (e.g. FkpA-p24/CTD-biotin and Skp-p24/CTD-ruthenium). Preliminary data suggest that the use of oligomeric p24 variants ensures an excellent seroconversion sensitivity which is unmatched by competitor assays.

The invention therefore concerns soluble HTLV p24 antigens that comprise either the N-terminal domain and lack the C-terminal domain or that comprise the C-terminal domain of the full-length HTLV p24 polypeptide and lack the N-terminal domain, respectively. According to the invention the p24 antigens can be fused to chaperones. Also encompassed is the use of these HTLV p24 antigens in diagnostic applications such as immunoassays for detecting antibodies against HTLV-I or HTLV-II in an isolated biological sample. The term "HTLV" means "human T-cell lymphotropic virus". Unless specifically marked as HTLV-I or HTLV-II the term HTLV refers to both virus types.

According to the invention the antigen comprises only a certain domain of the complete HTLV p24 antigen such as the N-terminal domain (NTD) or the C-terminal domain (CTD). Preferably, the antigen comprises the N-terminal domain of SEQ ID NO. 2 or the C-terminal domain of SEQ ID NO. 3 of HTLV-I p24. For the HTLV-II antigen, the fusion antigen preferably comprises the N-terminal domain of SEQ ID NO. 6 or the C-terminal domain of SEQ ID. NO. 7. In a further preferred mode, if the N-terminal domain is part of the antigen the C-terminal domain is missing and vice versa.

In particular, the invention concerns a soluble HTLV p24 antigen comprising the N-terminal domain (NTD) of HTLV p24 as specified in SEQ ID NO. 2 (p24 NTD HTLV-I) or SEQ ID NO. 6 (p24 NTD HTLV-II) wherein said HTLV p24 antigen lacks the C-terminal domain (CTD) as specified in SEQ ID NO. 3 (p24 CTD HTLV-I) and in SEQ ID NO. 7 (p24 CTD HTLV-II).

In addition, the invention concerns a soluble HTLV p24 antigen comprising the C-terminal domain of HTLV p24 as specified in SEQ ID NO. 3 (p24 CTD HTLV-I) or SEQ ID NO. 7 (p24 CDT HTLV-II) wherein said HTLV p24 antigen lacks the N-terminal domain as specified in SEQ ID NO. 2 (p24 NTD HTLV-I) and in SEQ ID NO. 6 (p24 NTD HTLV-II).

The term HTLV p24 antigen encompasses also variants. HTLV p24 variants may easily be created by a person skilled in the art by conservative or homologous substitutions of the disclosed amino acid sequences (such as e.g. substitutions of a cysteine by alanine or serine). The term "variants" in this context also relates to a protein or a protein fragment (i.e. a polypeptide or peptide) substantially similar to said protein. For example, modifications such as C- or N-terminal truncations by 1 to 10 amino acids are within the scope of the claimed HTLV p24 antigens. In particular, a variant may be an isoform which shows amino acid exchanges, deletions or insertions compared to the amino acid sequence of the most prevalent protein isoform. In one embodiment, such a substantially similar protein has a sequence similarity to the most prevalent isoform of the protein of at least 80%, in another embodiment at least 85% or at least 90%, in yet another embodiment at least 95%. The term "variant" also relates to a post-translationally modified protein such as a glycosylated or phosphorylated protein. According to the invention a variant classifies as a HTLV p24 antigen variant as long as the immunoreactivity in an in vitro diagnostic immunoassay is maintained, i.e. the variant is still able to bind and detect anti-HTLV p24 antibodies present in an isolated sample. A "variant" is also a protein or antigen which has been modified for example by covalent or non-covalent attachment of a label or carrier moiety to the protein or antigen. Possible labels are radioactive, fluorescent, chemiluminescent, electrochemiluminescent, enzymes or others e.g. like digoxigenin or biotin. These labels are known to a person skilled in the art.

The HTLV p24 antigens of the current invention are soluble, stable and immunoreactive, i.e. they are suitable as antigens for use in an immunological assay. This means that the antigens according to the invention are soluble under physiological buffer conditions, for example in a phosphate buffer system at ambient temperature without addition of detergents. The antigens are also capable of binding to or being recognized and bound by antibodies specific for HTLV p24, like e.g. anti-p24 antibodies present in an isolated sample such as human sera.

The HTLV p24 antigens according to the invention may be fused to a chaperone. The term "fusion protein", "fusion polypeptide" or "fusion antigen" as used in the present invention refers to a protein comprising at least one protein part corresponding to a HTLV p24 polypeptide and at least one protein part derived from a chaperone that serves the role of a fusion partner.

Chaperones, which are known as classical folding helpers, are proteins that assist the folding and maintenance of the structural integrity of other proteins. Examples of folding helpers are described in detail in WO 03/000877. According to the invention chaperones of the peptidyl prolyl isomerase class such as chaperones of the FKBP family can be used for fusion to the HTLV p24 antigen variants. Examples of FKBP chaperones suitable as fusion partners are FkpA, SlyD and SlpA. A further chaperone suitable as a fusion partner for HTLV p24 is Skp, a trimeric chaperone from the periplasm of E. coli, not belonging to the FKBP family. It is not always necessary to use the complete sequence of a chaperone. Functional fragments of chaperones (so-called binding-competent modules) which still possess the required abilities and functions may also be used (cf. WO 98/13496).

According to a further embodiment of the invention at least one or at least two modules of an FKBP chaperone such as e.g. E. coli SlyD, SlpA or FkpA are used as fusion moieties for expression of the HTLV p24 antigens. The chaperone Skp may be used as a fusion partner as well. The fusion of two FKBP-chaperone domains results in improved solubility of the resulting fusion polypeptide. The fusion moieties may be located at the N-terminus or at the C-terminus or at both ends (sandwich-like) of the HTLV p24 antigen.

Preferably, the HTLV p24 antigens according to the invention are fused to an oligomeric chaperone. Oligomeric chaperones are chaperones that naturally form dimers, trimers or even higher multimers so that a plurality of monomeric subunits are assembled by specific non-covalent interactions. Preferred oligomeric chaperones are FkpA and Skp.

Particularly preferred is a soluble HTLV p24 antigen fused to a chaperone selected from the group consisting of SEQ ID NOs. 9 to 16 and 18 to 24.

The HTLV p24 antigens according to the invention can be generated and prepared by means of recombinant DNA techniques. Another aspect of the invention therefore is a recombinant DNA molecule encoding a HTLV p24 antigen and variants thereof as defined further above.

The term "recombinant DNA molecule" refers to a molecule which is made by the combination of two otherwise separated segments of DNA sequence accomplished by the artificial manipulation of isolated segments of polynucleotides by genetic engineering techniques or by chemical synthesis. In doing so one may join together polynucleotide segments of desired functions to generate a desired combination of functions. Recombinant DNA techniques for expression of proteins in prokaryotic or lower or higher eukaryotic host cells are well known in the art. They have been described e.g. by Sambrook et al., (1989, Molecular Cloning: A Laboratory Manual)

The recombinant DNA molecules according to the invention may also contain sequences encoding linker peptides of 10 to 100 amino acid residues in between the HTLV p24 antigen and the fusion moieties and also between several fusion moieties. Such a linker sequence may for example harbor a proteolytic cleavage site.

A further aspect of the invention is an expression vector comprising operably linked a recombinant DNA molecule according to the present invention, i.e., a recombinant DNA molecule encoding an HTLV p24 antigen and optionally a peptidyl prolyl isomerase chaperone, such as an FKBP-chaperone, wherein the FKBP-chaperone is selected from FkpA, SlyD and SlpA. In an alternative embodiment the recombinant DNA molecule encodes a fusion protein comprising an HTLV p24 antigen and Skp. The expression vector comprising a recombinant DNA according to the present invention may be used to express the HTLV p24 antigen in a cell free translation system or may be used to transform a host cell for expression of the HTLV p24 antigen according to methods well known in the art. Another aspect of the invention therefore relates to a host cell transformed with an expression vector according to the present invention. In one embodiment of the current invention the recombinant HTLV p24 antigens are produced in *E. coli* cells.

An additional aspect is a method for producing a soluble, stable and immunoreactive HTLV p24 antigen according to the invention. Said p24 antigen may be produced as a fusion protein containing the HTLV p24 antigen and a chaperone. Preferably, a chaperone such as Skp or a peptidyl prolyl isomerase class chaperone like an FKBP chaperone is used. In a further embodiment of the invention said FKBP chaperone is selected from the group consisting of SlyD, FkpA and SlpA.

This method comprises the steps of a) culturing host cells transformed with the above-described expression vector containing a gene encoding an HTLV p24 antigen b) expression of the gene encoding said HTLV p24 antigen c) purification of said HTLV p24 antigen.

Optionally, as an additional step d), functional solubilization needs to be carried out so that the HTLV p24 antigen is brought into a soluble and immunoreactive conformation by means of refolding techniques known in the art.

An additional aspect of the present invention concerns a method for the detection of anti-HTLV antibodies in an isolated human sample wherein an HTLV p24 antigen according to the invention is used as a binding partner for the antibodies. The invention thus covers a method for the detection of antibodies specific for HTLV in an isolated sample, said method comprising a) forming an immunoreaction admixture by admixing a body fluid sample with an HTLV p24 antigen according to the invention b) maintaining said immunoreaction admixture for a time period sufficient for allowing antibodies against said HTLV p24 antigen present in the body fluid sample to immunoreact with said HTLV p24 antigen to form an immunoreaction product; and c) detecting the presence and/or the concentration of any of said immunoreaction product.

In a further aspect said method is suitable for detecting HTLV antibodies of the IgG and the IgM subclass.

Immunoassays for detection of antibodies are well known in the art, and so are methods for carrying out such assays and practical applications and procedures. The HTLV p24 antigens according to the invention can be used to improve assays for the detection of anti-HTLV antibodies independently of the labels used and independently of the mode of detection (e.g., radioisotope assay, enzyme immunoassay, electrochemiluminescence assay, etc.) or the assay principle (e.g., test strip assay, sandwich assay, indirect test concept or homogenous assay, etc.). All biological liquids known to the expert can be used as isolated samples for the detection of anti-HTLV antibodies. The samples usually used are bodily liquids like whole blood, blood sera, blood plasma, urine or saliva.

A further embodiment of the invention is an immunoassay for detecting anti-HTLV antibodies in an isolated sample performed according to the so-called double antigen sandwich concept (DAGS). Sometimes this assay concept is also termed double antigen bridge concept, because the two antigens are bridged by an antibody analyte. In such an assay the ability of an antibody to bind at least two different molecules of a given antigen with its two (IgG, IgE), four (IgA) or ten (IgM) paratopes is required and utilized.

In more detail, an immunoassay for the determination of anti-HTLV antibodies according to the double antigen bridge format is carried out by incubating a sample containing the anti-HTLV antibodies with two different HTLV p24 antigens, i.e. a first ("solid phase") HTLV p24 antigen and a second HTLV p24 ("detection") antigen, wherein each of the said antigens binds specifically to said anti-HTLV antibodies. The first antigen can be bound directly or indirectly to a solid phase and usually carries an effector group which is part of a bioaffine binding pair like, e.g., biotin and avidin. For example, if the first antigen is conjugated to biotin the solid phase is coated with either avidin or streptavidin. The second antigen carries a label. Thus an immuno-reaction admixture is formed comprising the first antigen, the sample antibody and the second antigen. A solid phase to which the first antigen can be bound is added either before the addition of the sample to said antigens or after the immunoreaction admixture is formed. This immunoreaction admixture is maintained for a time period sufficient for allowing anti-HTLV antibodies against said HTLV p24 antigens in the body fluid sample to immunoreact with said HTLV p24 antigens to form an immunoreaction product. Next step is a separation step wherein the liquid phase is separated from the solid phase. Finally, the presence of any of said immunoreaction product is detected in the solid or liquid phase or both.

In said DAGS immunoassay the basic structures of the "solid phase antigen" and the "detection antigen" are essentially the same. It is also possible to use, in a double antigen bridge assay, similar but different HTLV p24 antigens, which are immunologically cross-reactive. The essential requirement for performing such assays is that the relevant epitope or the relevant epitopes are present on both antigens. According to the invention it is possible to use different fusion moieties for each HTLV p24 antigen (e.g. SlyD fused to HTLV p24 on the solid phase side and FkpA p24 fused to HTLV p24 on the detection side) as such variations significantly alleviate the problem of non-specific binding and thus mitigate the risk of false-positive results.

Preferably, in said DAGS immunoassay an asymmetric format is applied, combining an HTLV p24 fused to FkpA and an HTLV p24 antigen fused to Skp. More preferably, the HTLV p24 fused to FkpA is used on the solid phase side and the HTLV p24 fused to Skp is applied on the detection side but it is also possible to have a reversed arrangement, i.e. an HTLV p24 antigen fused to Skp on the solid phase side and the HTLV p24 fused to FkpA on the detection side. Most preferably, the HTLV p24 FkpA fusion protein carries a biotin moiety for attachment to a solid phase that has been coated with streptavidin or avidin and the HTLV p24 Skp fusion protein carries an electrochemiluminescent label such as ruthenium complexes. In case of a reversed arrangement the p24 Skp fusion protein carries a biotin and the p24 FkpA carries said label.

A further embodiment of the present invention is therefore an immunoassay according to the double antigen bridge concept wherein a first HTLV p24 antigen according to the present invention, and a second HTLV p24 antigen according to the present invention are used.

The present invention further relates to the use of at least one antigen of HTLV p24 in a diagnostic test for the detection of anti-HTLV antibodies.

An additional subject matter of the invention is a reagent kit for the detection of antibodies against HTLV, containing, in addition to the usual test additives for immunoassays, at least one antigen of the HTLV p24 antigens according to the invention suitable for specifically binding to HTLV antibodies to be determined and possibly carrying a label as well as other usual additives if necessary.

Further subject matter of the invention is a reagent kit for the detection of anti-HTLV antibodies, comprising at least an HTLV p24 antigen or an HTLV antigen composition.

In particular the reagent kit contains an HTLV p24 antigen according to any of SEQ ID NOs. 9 to16 and 18 to 24.

In addition, the reagent kits defined above contain controls and standard solutions as well as reagents in one or more solutions with the common additives, buffers, salts, detergents etc. as used by the average man skilled in the art along with instructions for use.

Another embodiment is a composition of HTLV antigens comprising a soluble HTLV p24 antigen according to the current invention and an HTLV env antigen, preferably gp21 comprising SEQ ID NO. 25. The term "composition" refers to separately expressed polypeptides that are present as individual distinct molecules in a mixture. The term composition excludes a protein that bears p24 and gp21 fragments on a single polypeptide chain.

Preferred is a composition comprising the C-terminal domains of HTLV p24, particularly preferred is a composition comprising an HTLV-I p24 antigen according to SEQ ID NO. 3 (lacking SEQ ID NO. 2) and/or an HTLV-II p24 antigen according to SEQ ID NO. 7 (lacking SEQ ID NO. 6) and HTLV gp21. For example, in said composition an HTLV gp21 sequence comprising any of SEQ ID NOs. 25, 26 or 27 can be present. For application in an immunoassay according to the DAGS format the composition comprises each HTLV antigen in two forms, i.e. in a form that enables the antigen to be attached to a solid phase (e.g. a biotinylated antigen that can bind to a surface coated with streptavidin) and in a labeled form that enables detection of the immunocomplex between HTLV antibodies present in the sample and the applied HTLV antigens.

The invention also concerns the use of a HTLV p24 antigen according to the invention in an in vitro diagnostic test for the detection of anti-HTLV antibodies.

The invention is further illustrated by the Examples.

Example 1

Cloning and Purification of p24 Capsid Fusion Polypeptides

Cloning of Expression Cassettes

On the basis of the pET24a expression plasmid of Novagen (Madison, Wis., USA), expression cassettes encoding p24 fusion proteins from HTLV-I and HTLV-II were obtained essentially as described (Scholz, C. et al., J. Mol. Biol. (2005) 345, 1229-1241). The sequences of the p24 antigens from HTLV-I and HTLV-II were retrieved from the SwissProt database (SwissProt ID P10274 and P03353, respectively). A synthetic gene encoding p24 capsid antigen aa 146-344 (numbering refers to the Gag-Pro polyprotein precursor) from HTLV-I (lacking the proline-rich 15 amino acids at the N-terminus of the mature capsid protein) with a glycine-rich linker region fused in frame to the N-terminus was purchased from Medigenomix (Martinsried, Germany). The cysteine residues of p24 at positions 193, 311 and 332 were changed to alanine residues in order to prevent unwanted side-effects such as oxidation or intermolecular disulfide bridging. BamHI and XhoI restriction sites were at the 5' and the 3' ends of the p24-coding region, respectively. A further synthetic gene encoding two EcSlyD units (residues 1-165 of SwissProt accession no. P0A9K9) connected via a glycine-rich linker region and encompassing part of a further linker region at the C-terminus were likewise purchased from Medigenomix. NdeI and BamHI restriction sites were at the 5' and 3' ends of this cassette, respectively. The genes and the restriction sites were designed to enable the in frame fusion of the chaperone part EcSlyD-EcSlyD and the p24 antigen part by simple ligation. In order to avoid inadvertent recombination processes and to increase the genetic stability of the expression cassette in the *E. coli* host, the nucleotide sequences encoding the EcSlyD units were degenerated as were the nucleotide sequences encoding the extended linker regions. i.e., different codon combinations were used to encode identical amino acid sequences.

The pET24a vector was digested with NdeI and XhoI and the cassette comprising tandem-SlyD fused in frame to HTLV-I p24 (146-344) was inserted. Expression cassettes comprising *Pasteurella multocida* SlyD (1-156, SwissProt ID Q9CKP2) *E. coli* Skp (21-161, SwissProt ID POAEU7) or *E. coli* FkpA (26-270, SwissProt ID P45523) were constructed accordingly, as well as expression cassettes comprising p24 and p24 fragments from HTLV-II (SwissProt ID P03353). As with p24 from HTLV-I, the genuine cysteine residues of p24 from HTLV-II at positions 199, 281, 317 and 338 (again, numbering refers to the precursor Gag-Pro polyprotein) were changed to alanine residues in order to prevent unwanted side-effects such as oxidation or intermolecular disulfide bridging. All recombinant fusion polypeptide variants contained a C-terminal hexahistidine tag to facilitate Ni-NTA-assisted purification and refolding. QuikChange (Stratagene, La Jolla, Calif., USA) and standard PCR techniques were used to generate point mutations, deletion, insertion and extension variants or restriction sites in the respective expression cassettes.

The drawing below shows a scheme of the N-terminally truncated HTLV-I p24 antigen 146-344 bearing two SlyD chaperone units fused in frame to its N-terminal end. To denote the *E. coli* origin of the SlyD fusion partner, the depicted fusion polypeptide has been named EcSlyD-EcSlyD-p24 (146-344).

| Nde I | | | | BamH I | | Xho I |
|---|---|---|---|---|---|---|
| Ec SlyD (1-165) | L | Ec SlyD (1-165) | L | p24 (146-344) | | |

L = (GGGS)$_5$GGG-Linker

The insert of the resulting plasmid was sequenced and found to encode the desired fusion protein. The complete amino acid sequences of the p24 fusion polypeptides from HTLV-I and HTLV-II are shown in SEQ ID NOs. 9 to 16 and 18 to 24. The amino acid sequence of the linker L is shown is SEQ ID NO. 17.

Purification of fusion proteins comprising p24 and p24 variants from HTLV-I and HTLV-II All p24 fusion protein variants were purified by using virtually identical protocols. E. coli BL21 (DE3) cells harboring the particular pET24a expression plasmid were grown at 37° C. in LB medium plus kanamycin (30 μg/ml) to an $OD_{600}$ of 1.5, and cytosolic overexpression was induced by adding 1 mM isopropyl-β-D-thiogalactoside. Three hours after induction, cells were harvested by centrifugation (20 min at 5000 g), frozen and stored at −20° C. For cell lysis, the frozen pellet was resuspended in chilled 50 mM sodium phosphate pH 8.0, 7.0 M GdmCl, 5 mM imidazole and the suspension was stirred for 2 h on ice to complete cell lysis. After centrifugation and filtration (0.45 μm/0.2 μm), the crude lysate was applied onto a Ni-NTA column equilibrated with the lysis buffer including 5.0 mM TCEP. The subsequent washing step was tailored for the respective target protein and ranged from 5 to15 mM imidazole (in 50 mM sodium phosphate pH 8.0, 7.0 M GdmCl, 5.0 mM TCEP). At least 10-15 volumes of the washing buffer were applied. Then, the GdmCl solution was replaced by 50 mM potassium phosphate pH 8.0, 100 mM KCl, 10 mM imidazole, 5.0 mM TCEP to induce conformational refolding of the matrix-bound protein. In order to avoid reactivation of copurifying proteases, a protease inhibitor cocktail (Complete® EDTA-free, Roche) was included in the refolding buffer. A total of 15-20 column volumes of refolding buffer were applied in an overnight reaction. Then, both TCEP and the Complete® EDTA-free inhibitor cocktail were removed by washing with 3-5 column volumes 50 mM potassium phosphate pH 8.0, 100 mM KCl, 10 mM imidazole. Subsequently, the imidazole concentration—still in 50 mM potassium phosphate pH 8.0, 100 mM KCl—was raised to 20-80 mM (depending on the respective target protein) in order to remove unspecifically bound protein contaminants. The native protein was then eluted by 500 mM imidazole in the same buffer. Protein-containing fractions were assessed for purity by Tricine-SDS-PAGE and pooled. Finally, the proteins were subjected to size-exclusion-chromatography (Superdex HiLoad, Amersham Pharmacia) and the protein-containing fractions were pooled and concentrated to 10-20 mg/ml in an Amicon cell (YM10).

After the coupled purification and refolding protocol, protein yields of roughly 10-30 mg could be obtained from 1 g of E. coli wet cells, depending on the respective target protein.

Example 2

Spectroscopic Measurements

Protein concentration measurements were performed with an Uvikon XL double-beam spectrophotometer. The molar extinction coefficients ($\varepsilon_{280}$) were determined by using the procedure described by Pace (1995), Protein Sci. 4, 2411-2423. The molar extinction coefficients ($\varepsilon_{M280}$) used for the distinct fusion polypeptides are specified in table 1.

TABLE 1

Protein parameters of the p24 fusion polypeptide variants generated and used in this study. All parameters are referring to the respective protein monomers.

| fusion protein | length of target protein (aa residues) | molecular weight of fusion polypeptide (Da) | pI | $\varepsilon_{M280}$ $m^{-1}cm^{-1}$ | $Abs_{0.1\%}$ (= 1 mg/ml) |
|---|---|---|---|---|---|
| p24 variants HTLV-I | | | | | |
| EcSlyD-EcSlyD-p24 | 146-344 | 61762 | 5.0 | 35870 | 0.581 |
| EcFkpA-p24 | 146-344 | 50840 | 6.8 | 39880 | 0.784 |
| EcSkp-p24 | 146-344 | 40306 | 9.1 | 25440 | 0.631 |
| EcSlyD-EcSlyD-p24/CTD | 258-344 | 49311 | 4.9 | 25900 | 0.525 |
| EcFkpA-p24/CTD | 258-344 | 38389 | 7.1 | 29910 | 0.779 |
| EcSkp-p24/CTD | 258-344 | 27855 | 9.3 | 15470 | 0.555 |
| EcSlyD-EcSlyD-p24/NTD | 146-260 | 52486 | 4.8 | 21890 | 0.417 |
| EcFkpA-p24/NTD | 146-260 | 41565 | 6.5 | 25900 | 0.623 |
| EcSkp-p24/NTD | 146-260 | 31031 | 9.0 | 11460 | 0.369 |
| p24 variants HTLV-II | | | | | |
| EcSlyD-EcSlyD-p24 | 152-350 | 61868 | 5.0 | 35870 | 0.580 |
| EcFkpA-p24 | 152-350 | 50946 | 7.2 | 39880 | 0.783 |
| EcSkp-p24 | 152-350 | 40412 | 9.2 | 25440 | 0.630 |
| EcFkpA-p24/CTD | 267-350 | 38120 | 7.1 | 29910 | 0.785 |
| EcSkp-p24/CTD | 267-350 | 27586 | 9.3 | 15470 | 0.561 |
| EcFkpA-p24/NTD | 152-266 | 41739 | 6.7 | 25900 | 0.621 |
| EcSkp-p24/CTD | 152-266 | 31205 | 9.2 | 11460 | 0.367 |

The amino acid sequences of the fusion polypeptide variants are shown in SEQ ID NOs. 9 to 16 and 18 to 24.

Example 3

Coupling of Biotin and Ruthenium Moieties to the Fusion Proteins

The lysine ε-amino groups of the fusion polypeptides were modified at protein concentrations of 10-30 mg/ml with N-hydroxy-succinimide activated biotin and ruthenium label molecules, respectively. The label/protein ratio varied from 2:1 to 5:1 (mol:mol), depending on the respective fusion protein. The reaction buffer was 150 mM potassium phosphate pH 8.0, 100 mM KCl, 0.5 mM EDTA. The reaction was carried out at room temperature for 15 min and stopped by adding buffered L-lysine to a final concentration of 10 mM. To avoid hydrolytic inactivation of the labels, the respective stock solutions were prepared in dried DMSO (seccosolv quality, Merck, Germany). DMSO concentrations up to 25% in the reaction buffer were well tolerated by all fusion proteins studied. After the coupling reaction, unreacted free label was removed by passing the crude protein conjugate over a gel filtration column (Superdex 200 HiLoad).

Example 4

Immunological Reactivity (i.e., Antigenicity) of Different p24 Capsid Antigen Variants in a HTLV Immunoassay The immunological reactivity (antigenicity) of the polypeptide fusion variants of HTLV p24 capsid antigen was assessed in automated Elecsys® 2010 and cobas e 411 analyzers (Roche Diagnostics GmbH). Elecsys® is a registered trademark of the Roche group. Measurements were carried out in the double antigen sandwich format.

Signal detection in Elecsys® 2010 and cobas e 411 is based on electrochem (i.e. the capture-antigen) is immobilized on the surface of a streptavidin coated magnetic bead whereas the detection-antigen bears a complexed Ruthenium cation (switching between the redox states 2 +and 3+) as the signaling moiety. In the presence of a specific immunoglobulin analyte, the chromogenic ruthenium complex is bridged to the solid phase and emits light at 620 nm after excitation at a platinum electrode. The signal output is in relative light units.

The recombinant p24 capsid antigen fusion polypeptides were assessed in a double antigen sandwich (DAGS) immunoassay format. To this end, recombinant HTLV-I capsid antigen p24 was used as a biotin and a ruthenium conjugate, respectively, to detect anti-p24 antibodies in human sera.

p24 is one of the immunodominant antigens of HTLV, and soluble variants of p24—as disclosed in this patent application—are invaluable tools for the detection of HTLV infections. In all measurements, chemically polymerized and unlabeled EcSlyD-EcSlyD, EcFkpA and EcSkp were implemented in large excess (~10 µg/ml) in the reaction buffer as anti-interference substances to avoid immunological cross reactions via the chaperone fusion units.

In particular, three p24 variants from HTLV-I were scrutinized in this study, namely full length p24 (146-344, numbering refers to Gag-Pro polyprotein precursor, see SEQ ID NOs. 1 and 5), p24 N-terminal domain (p24/NTD, 146-260) and p24 C-terminal domain (p24/CTD, 261-344). In order to detect anti-p24 IgG molecules, EcSlyD-EcSlyD-p24-biotin and EcSlyD-EcSlyD-p24-ruthenium were used in R1 (reagent buffer 1) and R2 (reagent buffer 2), respectively. In order to detect both anti-p24 IgM and IgG molecules, EcFkpA-p24-biotin and EcSkp-p24-ruthenium were used in R1 (reagent buffer 1) and R2 (reagent buffer 2), respectively. The concentrations of the antigen conjugates in R1 and R2, respectively, were 100 ng/ml each. N-terminally truncated mature p24 (146-344) was used as an EcSlyD-EcSlyD fusion polypeptide on the biotin-side and as an EcFkpA fusion polypeptide on the ruthenium side.

Unfortunately, human HTLV seroconversion panels—which are an indispensable tool for the development of improved in vitro diagnostic assays—are not available commercially. In order to assess the antigenic properties of the different p24 variants in the very early phase of HTLV infection, we had to recur to rabbit sera serving as a seroconversion model. To this end, New Zealand White Rabbits were immunized with purified and inactivated HTLV-I and -II viral lysates (purchased from Zeptometrix, New York, USA) and complete Freund's adjuvant to induce an immune response (2 immunizations, 1 week interval). We are aware that the pattern of the humoral immune response upon true HTLV infections in man might slightly differ from an immune response triggered by virus lysate vaccination of rabbits. Yet, the artificially induced rabbit seroconversion is the best mimic that was available to us.

In a first experiment, monomeric p24 CTD (p24, 261-344) was assessed with anti-HTLV-negative human sera in the aforementioned DAGS immunoassay setup in order to get an idea of the background signal. The unavoidable system-inherent signal is around 500 counts. Low background signals are indicative of high solubility and generally benign physicochemical properties of the respective ruthenium conjugates. From table 2 we can infer that the physicochemical properties of monomeric p24 CTD are excellent (column 1). This holds true for oligomeric p24 CTD as well (column 2): FkpA-p24(261-344)-biotin and Skp-p24(261-344)-ruthenium, when used as an antigen pair in the DAGS format, lead to a signal background of ~1100 counts with negative human sera, which clearly points to good solubility properties. However, it becomes evident at first glance that the monomeric and the oligomeric form of p24 CTD strongly differ in their capability to detect anti-HTLV-antibodies (and notably IgM molecules) in seroconversion panels as shown in Table 2. Having a closer look at seroconversion K5645, we find that monomeric p24 CTD barely detects day 18 as positive (1558 counts), whereas the use of oligomeric p24 CTD already reveals day 14 as clearly positive (8232 counts) and leads to a signal as high as 50118 counts at day 18. We see the same picture with seroconversion panels K5646, K5647 and K5648: the oligomeric p24 CTD variant produces higher signals at earlier times and thus warrants an excellent sensitivity in the early detection of anti-p24 antibodies in seroconversions. In principle, the situation is similar with the N-terminal domain (NTD) of p24, which encompasses the amino acid residues 146-260 (numbering refers to Gag-Pro polyprotein precursor). As with the CTD, the oligomeric form of p24 NTD is better suited to detect antibodies that appear in the early phase of seroconversion (i.e., immuno-globulins of the M-type), which is exemplified in particular with the seroconversion panels K5647 and K5648 (Table 2, columns 3 and 4). However, the background signals of the oligomeric NTD p24 are significantly increased when compared to CTD p24. In addition, the antigenicity of the C-terminal domain of p24 seems to outdistance the antigenicity of the N-terminal domain. In conclusion, the oligomeric C-terminal domain of p24 possesses outstanding physicochemical and superior antigenic properties making it an attractive candidate for HTLV serology. It is clearly superior to full-length p24 (146-344, numbering of Gag-pro polyprotein precursor) in terms of sensitivity in early IgM detection. Since the Skp fusion polypeptide of full length p24 (146-344) was not available as it significantly tended to aggregate, we were confined to SlyD-SlyD and FkpA fusion polypeptides of the p24 full-length version. When monomeric SlyD-SlyD-p24 (146-344) is used on the biotin side and oligomeric FkpA-p24 (146-344) is used on the ruthenium side of the DAGS format, the results are quite clear-cut: full-length p24 yields excellent signals in the late phases of the seroconversion panels, but it completely fails in early detection (table 2, column 5). Both oligomeric CTD p24 and NTD p24 are superior to the monomeric full-length variant, providing good evidence that sensitive early detection is mainly dependent on the epitope density of the p24 fragments used. It does not seem to be mandatory to offer the complete p24 sequence as a whole to get an excellent seroconversion sensitivity. Rather, epitopes in the N and C-domain of p24 are sufficient to warrant a sensitive and reliable detection of IgM molecules in the early phase of HTLV infection—provided that these epitopes are offered in an oligomeric form. By virtue of its superior solubility (as reflected in the low background signals) and its outstanding antigenicity, the C-terminal domain of p24 from HTLV-I holds promise as an invaluable ingredient in a HTLV immunoassay. This was somewhat unexpected: since the C-domain of the p24 capsid antigen is presumably involved in p24 oligomerization (Khorasanizadeh et al., J. Mol. Biol. (1999) 291, 491-505), we reasoned that the isolated C-domain could possibly tend to aggregation, at least it should be more difficult to handle than the N-domain. Moreover, our expectation was that the p24 C-domain which is largely hidden in the mature capsid particles would probably harbor less immunodominant epitopes than the well-accessible N-domain. To our surprise, the converse is true. Indeed, the N-domain of p24 is also well-suited as an antigen for HTLV-immunoassay, albeit it seems inferior to the C-terminal domain in terms of solubility and antigenicity. Table 2 shows the results for p24 variants from HTLV-I. We found virtually identical results for the corresponding p24 variants from HTLV-II. This is in line with our expectations since the amino acid sequences of p24 from HTLV-I and HTLV-II share 84% identity and 93% homology. The corresponding sequences for p24 from HTLV-II were 152-266 (N-domain, NTD), 267-350 (C-domain, CTD) and 152-350 (mature full-length p24), see also SEQ ID NOs. 5-8.

TABLE 2 superior immunoreactivity of oligomeric p24 variants in early HTLV infections (increased sensitivity in rabbit seroconversion panels).

| p24 variant (fragment length) | mono CTD (261-344) | oligo CTD (261-344) | mono NTD (146-260) | oligoNTD (146-260) | Full-length p24 (146-344) |
|---|---|---|---|---|---|
| fusion partner R1 (Bi) | SlyD-SlyD | FkpA | SlyD-SlyD | FkpA | SlyD-SlyD |
| fusion partner R2 (Ru) | SlyD-SlyD | Skp | SlyD-SlyD | Skp | FkpA |
| conc. (ng/ml) | 100 | 100 | 100 | 100 | 300 |
| counts in Elecsys analyzer (cobas e 411) | | | | | |
| anti-HTLV-negative sera | | | | | |
| 0701.1201.01 | 599 | 976 | 667 | 2846 | 1677 |
| 0701.1202.01 | 611 | 1116 | 724 | 4331 | 1981 |
| 0701.1203.01 | 592 | 1148 | 717 | 4860 | 1933 |
| seroconversion panels (day of bleeding) | | | | | |
| K5645 (day 0) | 725 | 1037 | 790 | 2330 | 1608 |
| K5645 (day 10) | 612 | 1196 | 758 | 2549 | 1613 |
| K5645 (day 14) | 642 | 8232 | 729 | 2690 | 2910 |
| K5645 (day 18) | 1558 | 50118 | 906 | 3071 | 15191 |
| K5646 (day 0) | 592 | 1045 | 728 | 2359 | 1580 |
| K5646 (day 11) | 636 | 1396 | 770 | 2779 | 1665 |
| K5646 (day 15) | 1425 | 13090 | 740 | 3084 | 1715 |
| K5646 (day 19) | 14080 | 106376 | 4342 | 6321 | 8832 |
| K5646 (day 23) | 109285 | 160403 | 33361 | 15881 | 76212 |
| K5647 (day 0) | 814 | 917 | 799 | 2295 | 1445 |
| K5647 (day 12) | 2620 | 95130 | 1100 | 19920 | 3606 |
| K5647 (day 16) | 159796 | 61639 | 19774 | 88453 | 339050 |
| K5647 (day 20) | 187997 | 63193 | 62381 | 99227 | 623586 |
| K5648 (day 0) | 572 | 848 | 737 | 2113 | 1467 |
| K(5648 (day 10) | 803 | 1003 | 871 | 2562 | 1512 |
| K5648 (day 14) | 2575 | 122993 | 972 | 4324 | 2733 |
| K5648 (day 18) | 10107 | 181988 | 4401 | 21689 | 10892 |
| K5648 (day 22) | 58656 | 352195 | 7844 | 16692 | 48125 |

Example 5

Combinations of oligomeric chaperone carrier proteins in an asymmetric double antigen sandwich format.

The immunoassay was essentially performed as described in Example 4. Oligomeric chaperones such as FkpA and Skp may be used advantageously as fusion partners in order to achieve a functional oligomerization of their respective client antigens. Fusion of FkpA or Skp to target proteins (i.e., their client or guest antigens) may yield well-defined oligomeric fusion polypeptides which are suited for the detection of IgM molecules in immunoassays. Here, we addressed the question whether there is a particularly preferred combination of Skp-X and FkpA-X fusion polypeptides when used in a DAGS (double antigen sandwich) format. (Note: “X” generally refers to any target protein or antigen.) In other words, we addressed the question whether it is advisable to use FkpA-X fusion polypeptides on the (capture) biotin side rather than on the (signaling) ruthenium side. Conversely, we wondered whether it is advisable to use Skp-X fusion polypeptides on the (signaling) ruthenium side rather than on the (capture) biotin side.

In a first experiment, biotin and ruthenium conjugates of purified recombinant EcSkp and EcFkpA were prepared as described in example 3. That is, the purified chaperones (i.e., the naked chaperones without any fused target sequences) were biotinylated by means of an N-hydroxy-succinimide-activated biotin label. As well, ruthenylated chaperones (i.e., the naked chaperones without any fused target sequences) were produced by means of an N-hydroxy-succinimide-activated ruthenium label.

Then, a symmetric DAGS was performed with EcSkp on both the biotin and the ruthenium side at varying concentrations. As a sample, a pool of anti-HTLV negative human sera was used, and measurements were carried out in duplicate. It is obvious from the data in table 3, that the background signal is fairly high when using the very same oligomeric chaperone (here: EcSkp) on both the biotin and the ruthenium side of a DAGS format, even at very low concentrations. The background signal strongly increases with the conjugate concentration in a dose-dependent fashion. Thus, a symmetric DAGS format does not seem to be a viable option when using an oligomeric fusion partner such as the trimeric chaperone Skp from *E. coli*. Similar results have been found for the dimeric chaperone FkpA.

TABLE 3

Use of the very same oligomeric chaperone on both sides of a DAGS immunoassay (oligomeric carrier protein in symmetric DAGS format)

| Experiment | V1 | V2 | V3 | V4 | V5 | V6 |
|---|---|---|---|---|---|---|
| R1 basis buffer | | | | R1 | | |
| Skp-Bi conc. [ng/ml] | 10 | 20 | 50 | 100 | 250 | 500 |

TABLE 3-continued Use of the very same oligomeric chaperone on both sides of a DAGS immunoassay (oligomeric carrier protein in symmetric DAGS format)

| R2 basis buffer | R2 | | | | | |
|---|---|---|---|---|---|---|
| Skp-Ru conc. [ng/ml] | 10 | 20 | 50 | 100 | 250 | 500 |
| sample | Signal (counts) | Signal (counts) | Signal (counts) | Signal (counts) | Signal (counts) | Signal (counts) |
| Control 1 (Pool of anti-HTLV-negative human sera) | 3969 | 6301 | 12582 | 17521 | 21471 | 21498 |
| | 3921 | 6170 | 13187 | 17610 | 21467 | 22056 |

However, when we combined EcSkp and EcFkpA in an asymmetric DAGS format, the picture turned out completely different (see table 4 below). Irrespective of the combination of the chaperones, the background signals were substantially reduced when we used different chaperones on the capture and the signaling side. For instance, the background signal in the symmetric (i.e., Skp-Bi/Skp-Ru) DAGS format was around 21,000 counts at a conjugate concentration of 250 ng/ml each. At the very same conjugate concentration, the background signal in the asymmetric DAGS format is dramatically reduced to 2,700 counts (Skp-Bi/FkpA-Ru) and to 860 counts (FkpA-Bi/Skp-Ru), respectively. It is self-evident at first glance that there is, indeed, a preferred combination of FkpA and Skp in a DAGS immunoassay: it is advisable to use FkpA as a biotin conjugate and Skp as a ruthenium conjugate in a DAGS immunoassay, and it is reasonable to conclude that the same holds true for FkpA-X and Skp-X fusion polypeptides.

TABLE 4

Use of different oligomeric chaperones on both sides of a DAGS immunoassay (oligomeric carrier proteins in asymmetric DAGS format)

| Variant | V1 | V2 | V3 | V4 |
|---|---|---|---|---|
| R1 basis buffer | R1 | | | |
| R1 conc, [ng/ml] | Skp-Bi 10 | Skp-Bi 250 | FkpA-Bi 10 | FkpA-Bi 250 |
| R2 basis buffer | R2 | | | |
| R2 conc, [ng/ml] | FkpA-Ru 10 | FkpA-Ru 250 | Skp-Ru 10 | Skp-Ru 250 |
| sample | Signal (counts) | Signal (counts) | Signal (counts) | Signal (counts) |
| Control 1 | | | | |
| (Pool of anti-HTLVnegative human sera) | 567 561 | 2668 2764 | 447 439 | 854 864 |

Example 6

CD-detected Thermally Induced Unfolding of Skp-p24/CTD (267-350) and FkpA-p24/CTD (267-350)

Near-UV CD spectra were recorded with a Jasco-720 spectropolarimeter with a thermostatted cell holder and converted to mean residue ellipticity. The buffer was 150 mM potassium phosphate pH 8.0, 100 mM KCl, 0.5 mM EDTA. The pathlength was 0.2 cm, the protein concentration was 218 µM (referring to Skp-p24 monomer) or 147.5 µM (referring to FkpA-p24 monomer). The measuring range was 250-330 nm, the band width was 1.0 nm, the scanning speed was 20 nm/min at a resolution of 0.5 nm and the response was 1 s. In order to improve the signal-to-noise ratio, spectra were measured nine times and averaged.

Circular dichroism spectroscopy (CD) is the method of choice to assess both the secondary and the tertiary structure of proteins. Ellipticity in the aromatic region (250-330 nm) reports on tertiary contacts within a protein (i.e., the globular structure of a regularly folded protein) and is considered as the fingerprint region of a native-like fold (conformation).

Figure 3:
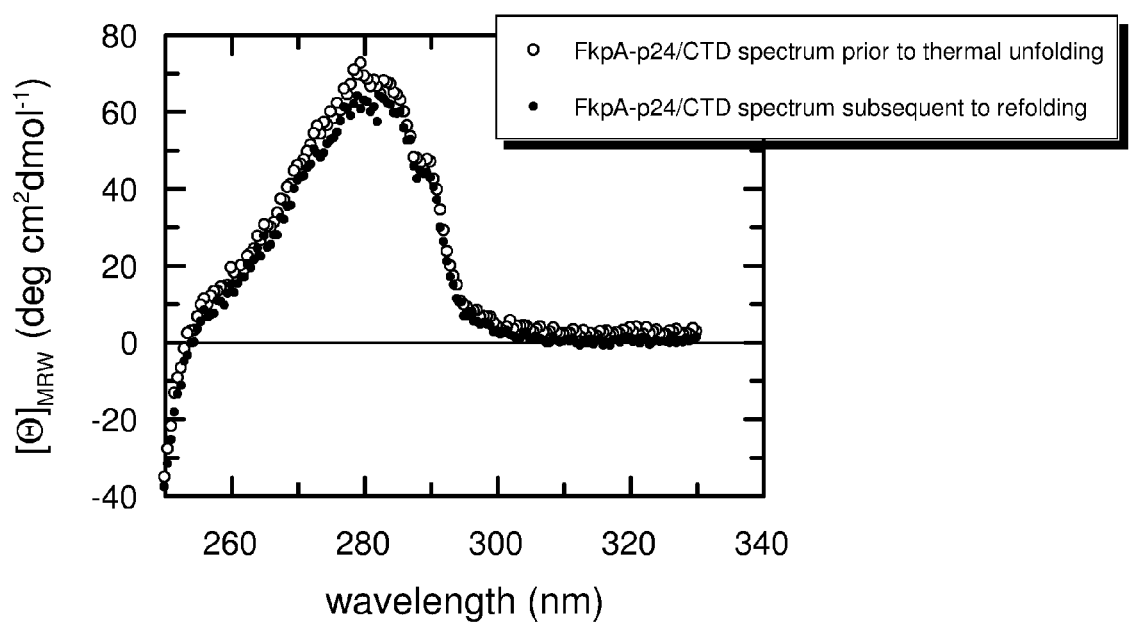

Near UV CD spectra of Skp-p24/CTD(267-350) and FkpA-p24/CTD(267-350), SEQ ID NO. 22 and 21, respectively, were monitored to address the question whether the fusion proteins adopt an ordered conformation after the matrix-coupled refolding procedure which is the crucial step in the purification process. The answer is quite clear-cut: the near UV CD signals of both Skp-p24/CTD (see FIG. 1) and FkpA-p24/CTD (see FIG. 3) unequivocally report an orderly tertiary structure of the respective fusion polypeptide. Obviously, the aromatic residues of Skp-p24/CTD and FkpA-p24/CTD are embedded in the lipophilic protein core and thus experience asymmetric surroundings which strongly points to a native-like conformation of the carrier and target protein component within the respective fusion construct. The near UV CD spectrum of Skp-p24/CTD exhibits a negative signal with maxima at 282 and 277 nm (FIG. 1). The near UV CD spectrum of FkpA-p24/CTD exhibits a positive signal with a maximum at 280 nm (FIG. 3).

In order to address the question whether the thermally induced unfolding of Skp-p24/CTD and FkpA-p24/CTD is reversible, melting curves were monitored in the near UV region at detection wavelengths of 277 and 280 nm, respectively. The temperature range was 20-75° C., the band width was 2.0 nm, the temperature slope was 1° C./min and the response was 2 s.

Figure 2:
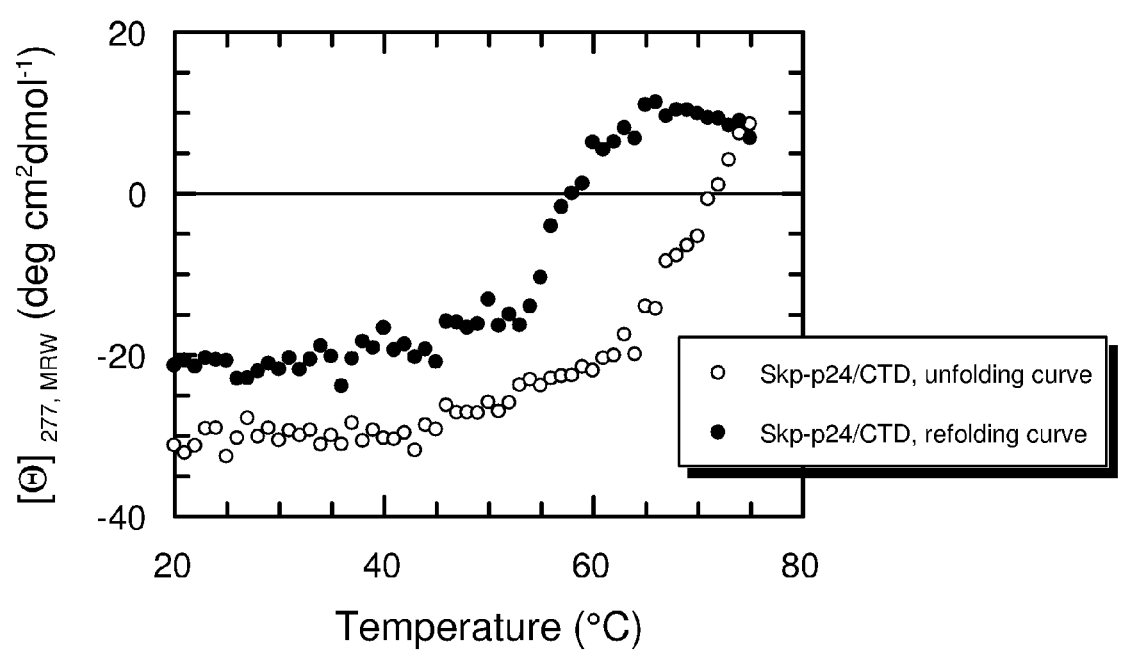
Figure 4:
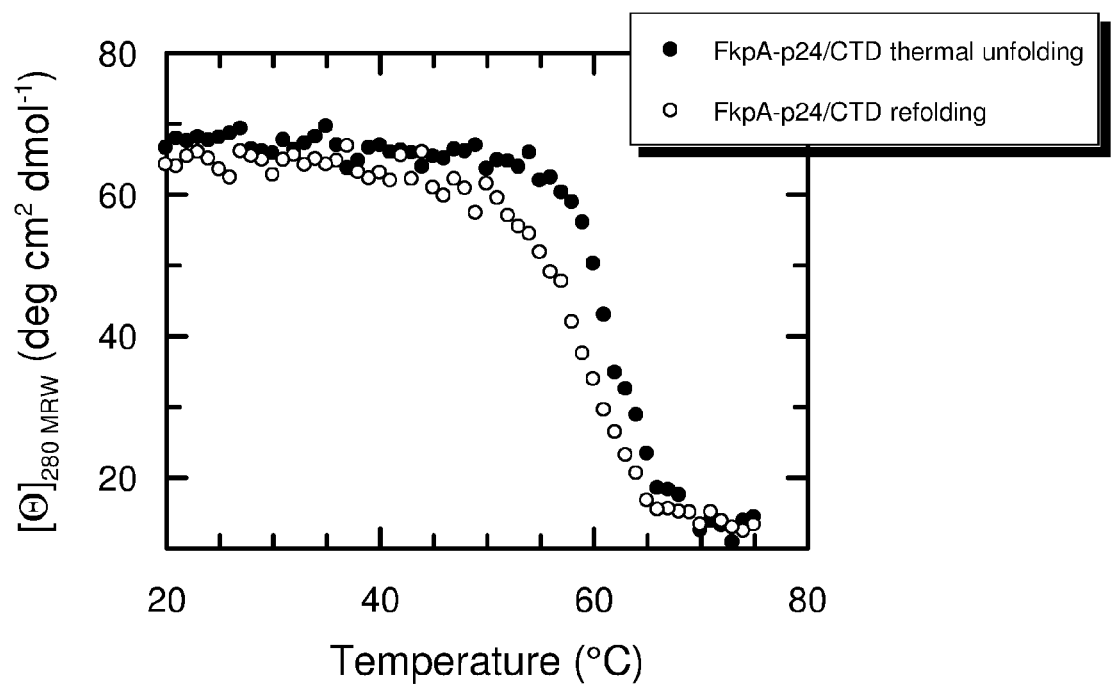

The thermally-induced unfolding was monitored at 277 and 280 nm, corresponding to the maximal signal amplitudes for Skp-p24/CTD and FkpA-p24/CTD, respectively. Upon heating, the non-covalent contacts which stabilize the native conformation of the fusion polypeptide molecules become loose and finally break down. For Skp-p24/CTD, this thermally induced unfolding (as monitored at 277 nm) is reflected in an increase in the CD signal as shown in FIG. 2. Skp-p24/CTD obviously retains its native-like fold and its trimeric structure up to 55° C. The onset of unfolding is between 55° C. and 60° C. At 70° C., the molecule is completely unfolded, as judged by the melting curve in FIG. 2. Strikingly, the CD signal is restored when the protein solution is chilled down to 20° C. (FIGS. 1, 2). Yet, the hysteresis of the refolding curve is pronounced and probably points to different pathways of unfolding and refolding. It is astounding that the thermally induced unfolding of a complex trimeric fusion protein such as Skp-p24/CTD is—at least partially—a reversible process. It would have been expected that Skp-p24/CTD, after thermally induced unfolding and dissociation into the monomeric subunits, would aggregate very quickly and quantitatively at an elevated temperature such as 75° C. Yet, we find that Skp-p24/CTD is obviously able to readopt its native-like conformation when the protein solution is chilled to 20° C. Indeed, the near UV CD spectra monitored before and after the thermally induced unfolding virtually superimpose (see FIG. 1). In conclusion, Skp-p24/CTD possesses robust folding properties which are outstanding for a molecule with this degree of complexity and which are highly desired for an antigen that is used in an immunoassay. We found very similar results for FkpA-p24/CTD: just like Skp-p24/CTD, FkpA-p24/CTD exhibits a marked CD signal in the near UV region (250-330 nm, signal maximum at 280 nm), pointing to a well-ordered conformation after the matrix-coupled refolding process (FIG. 3). The CD signal of FkpA-p24/CTD strongly decreases when the molecule unfolds and loses its tertiary structure (FIG. 4). By means of thermal transitions we observed that FkpA-p24/CTD indeed retains its native-like conformation at temperatures up to 55° C. The onset of unfolding—as monitored by near UV CD spectroscopy at 280 nm—is around 60° C., and at 70° C. FkpA-p24/CTD is fully unfolded. It is remarkable that the CD signal of the native FkpA-p24/CTD molecule is fully restored after a thermal unfolding/refolding cycle (FIG. 4). As illustrated in FIG. 3, the CD spectra of FkpA-p24/CTD before and after the unfolding/refolding cycle superimpose almost perfectly.

In conclusion, Skp-p24/CTD and FkpA-p24/CTD possess very robust folding properties which are outstanding for molecules with this degree of complexity and which are highly desirable for fusion polypeptides that serve as antigenic ingredients, i.e., specifiers in an immunoassay.

The invention claimed is:

1. A composition comprising an HTLV p24-chaperone fusion polypeptide comprising an N-terminal domain (NTD) of HTLV p24 selected from the group consisting of SEQ ID NO: 2 and SEQ ID NO: 6 wherein said HTLV p24 antigen lacks the C-terminal domain (CTD) selected from the group consisting of SEQ ID NO: 3 and in SEQ ID NO: 7; fused to an oligomeric chaperone, wherein the HTLV p24-chaperone fusion polypeptide in the composition is expressed as an individual distinct molecule.

2. The soluble HTLV p24 antigen according to claim 1, wherein the oligomeric chaperone is selected from the group consisting of Skp and FkpA.

3. A composition of HTLV antigens comprising the HTLV p24-chaperone fusion polypeptide according to claim 1 and an HTLV gp21 antigen comprising an amino acid sequence according to SEQ ID NO:25, wherein the HTLV p24-chaperone fusion polypeptide and the HTLV gp21 antigen are expressed as separate polypeptides.

4. The composition of claim 1, wherein the fusion polypeptide comprises an amino acid sequence according to SEQ ID NO: 14, 15, 16, 23, or 24 or a variant thereof that is at least 80% identical.

5. The composition of claim 1, wherein the fusion polypeptide comprises an amino acid sequence according to SEQ ID NO: 14, 15, 16, 23, or 24 or a variant thereof that is at least 90% identical.

6. The composition of claim 1, wherein the fusion polypeptide comprises an amino acid sequence according to SEQ ID NO: 14, 15, 16, 23, or 24 or a variant thereof that is at least 95% identical.

7. The composition of claim 3, wherein the fusion polypeptide comprises an amino acid sequence according to SEQ ID NO: 14, 15, 16, 23, or 24 or a variant thereof that is at least 80% identical.

8. The composition of claim 3, wherein the fusion polypeptide comprises an amino acid sequence according to SEQ ID NO: 14, 15, 16, 23, or 24 or a variant thereof that is at least 90% identical.

9. The composition of claim 3, wherein the fusion polypeptide comprises an amino acid sequence according to SEQ ID NO: 14, 15, 16, 23, or 24 or a variant thereof that is at least 95% identical.

\* \* \* \* \*

SEQUENCE LISTING

```
<160> NUMBER OF SEQ ID NOS: 27

<210> SEQ ID NO 1
<211> LENGTH: 199
<212> TYPE: PRT
<213> ORGANISM: Human T-cell lymphotropic virus type 1

<400> SEQUENCE: 1

Gln Met Lys Asp Leu Gln Ala Ile Lys Gln Glu Val Ser Gln Ala Ala
1               5                   10                  15

Pro Gly Ser Pro Gln Phe Met Gln Thr Ile Arg Leu Ala Val Gln Gln
            20                  25                  30

Phe Asp Pro Thr Ala Lys Asp Leu Gln Asp Leu Leu Gln Tyr Leu Cys
        35                  40                  45

Ser Ser Leu Val Ala Ser Leu His His Gln Gln Leu Asp Ser Leu Ile
50                  55                  60

Ser Glu Ala Glu Thr Arg Gly Ile Thr Gly Tyr Asn Pro Leu Ala Gly
65                  70                  75                  80

Pro Leu Arg Val Gln Ala Asn Asn Pro Gln Gln Gly Leu Arg Arg
            85                  90                  95

Glu Tyr Gln Gln Leu Trp Leu Ala Ala Phe Ala Ala Leu Pro Gly Ser
                100                 105                 110

Ala Lys Asp Pro Ser Trp Ala Ser Ile Leu Gln Gly Leu Glu Glu Pro
            115                 120                 125

Tyr His Ala Phe Val Glu Arg Leu Asn Ile Ala Leu Asp Asn Gly Leu
        130                 135                 140

Pro Glu Gly Thr Pro Lys Asp Pro Ile Leu Arg Ser Leu Ala Tyr Ser
145                 150                 155                 160

Asn Ala Asn Lys Glu Cys Gln Lys Leu Leu Gln Ala Arg Gly His Thr
                165                 170                 175

Asn Ser Pro Leu Gly Asp Met Leu Arg Ala Cys Gln Thr Trp Thr Pro
            180                 185                 190

Lys Asp Lys Thr Lys Val Leu
        195

<210> SEQ ID NO 2
<211> LENGTH: 115
<212> TYPE: PRT
<213> ORGANISM: Artificial
<220> FEATURE:
<223> OTHER INFORMATION: similar to human T-cell lymphotropic virus type
      1 but Xaa= Cys or Ala or Ser
<220> FEATURE:
<221> NAME/KEY: MISC_FEATURE
<222> LOCATION: (48)..(48)
<223> OTHER INFORMATION: Xaa = Cys or Ala or Ser

<400> SEQUENCE: 2

Gln Met Lys Asp Leu Gln Ala Ile Lys Gln Glu Val Ser Gln Ala Ala
1               5                   10                  15
```

```
Pro Gly Ser Pro Gln Phe Met Gln Thr Ile Arg Leu Ala Val Gln Gln
            20                  25                  30

Phe Asp Pro Thr Ala Lys Asp Leu Gln Asp Leu Leu Gln Tyr Leu Xaa
        35                  40                  45

Ser Ser Leu Val Ala Ser Leu His His Gln Gly Leu Asp Ser Leu Ile
 50                  55                  60

Ser Glu Ala Glu Thr Arg Gly Ile Thr Gly Tyr Asn Pro Leu Ala Gly
 65                  70                  75                  80

Pro Leu Arg Val Gln Ala Asn Asn Pro Gln Gln Gln Gly Leu Arg Arg
                85                  90                  95

Glu Tyr Gln Gln Leu Trp Leu Ala Ala Phe Ala Ala Leu Pro Gly Ser
            100                 105                 110

Ala Lys Asp
        115

<210> SEQ ID NO 3
<211> LENGTH: 84
<212> TYPE: PRT
<213> ORGANISM: Artificial
<220> FEATURE:
<223> OTHER INFORMATION: similar to human T-cell lymphotropic virus type
      1 but Xaa = Cys or Ala or Ser
<220> FEATURE:
<221> NAME/KEY: MISC_FEATURE
<222> LOCATION: (51)..(51)
<223> OTHER INFORMATION: Xaa = Cys or Ala or Ser
<220> FEATURE:
<221> NAME/KEY: MISC_FEATURE
<222> LOCATION: (72)..(72)
<223> OTHER INFORMATION: Xaa = Cys or Ala or Ser

<400> SEQUENCE: 3

Pro Ser Trp Ala Ser Ile Leu Gln Gly Leu Glu Glu Pro Tyr His Ala
 1               5                  10                  15

Phe Val Glu Arg Leu Asn Ile Ala Leu Asp Asn Gly Leu Pro Glu Gly
            20                  25                  30

Thr Pro Lys Asp Pro Ile Leu Arg Ser Leu Ala Tyr Ser Asn Ala Asn
        35                  40                  45

Lys Glu Xaa Gln Lys Leu Leu Gln Ala Arg Gly His Thr Asn Ser Pro
 50                  55                  60

Leu Gly Asp Met Leu Arg Ala Xaa Gln Thr Trp Thr Pro Lys Asp Lys
 65                  70                  75                  80

Thr Lys Val Leu

<210> SEQ ID NO 4
<211> LENGTH: 199
<212> TYPE: PRT
<213> ORGANISM: Artificial
<220> FEATURE:
<223> OTHER INFORMATION: similar to human T-cell lymphotropic virus type
      1 but Xaa = Cys or Ala or Ser
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: MISC_FEATURE
<222> LOCATION: (166)..(166)
<223> OTHER INFORMATION: Xaa = Cys or Ala or Ser
<220> FEATURE:
<221> NAME/KEY: MISC_FEATURE
<222> LOCATION: (187)..(187)
<223> OTHER INFORMATION: Xaa = Cys or Ala or Ser
```

<400> SEQUENCE: 4

```
Gln Met Lys Asp Leu Gln Ala Ile Lys Gln Glu Val Ser Gln Ala Ala
1               5                   10                  15

Pro Gly Ser Pro Gln Phe Met Gln Thr Ile Arg Leu Ala Val Gln Gln
            20                  25                  30

Phe Asp Pro Thr Ala Lys Asp Leu Gln Asp Leu Leu Gln Tyr Leu Xaa
        35                  40                  45

Ser Ser Leu Val Ala Ser Leu His His Gln Leu Asp Ser Leu Ile
50                  55                  60

Ser Glu Ala Glu Thr Arg Gly Ile Thr Gly Tyr Asn Pro Leu Ala Gly
65                  70                  75                  80

Pro Leu Arg Val Gln Ala Asn Asn Pro Gln Gln Gly Leu Arg Arg
                85                  90                  95

Glu Tyr Gln Gln Leu Trp Leu Ala Ala Phe Ala Ala Leu Pro Gly Ser
                100                 105                 110

Ala Lys Asp Pro Ser Trp Ala Ser Ile Leu Gln Gly Leu Glu Glu Pro
            115                 120                 125

Tyr His Ala Phe Val Glu Arg Leu Asn Ile Ala Leu Asp Asn Gly Leu
        130                 135                 140

Pro Glu Gly Thr Pro Lys Asp Pro Ile Leu Arg Ser Leu Ala Tyr Ser
145                 150                 155                 160

Asn Ala Asn Lys Glu Xaa Gln Lys Leu Leu Gln Ala Arg Gly His Thr
                165                 170                 175

Asn Ser Pro Leu Gly Asp Met Leu Arg Ala Xaa Gln Thr Trp Thr Pro
            180                 185                 190

Lys Asp Lys Thr Lys Val Leu
            195
```

<210> SEQ ID NO 5
<211> LENGTH: 199
<212> TYPE: PRT
<213> ORGANISM: Human T-cell lymphotropic virus type 2

<400> SEQUENCE: 5

```
Gln Met Lys Asp Leu Gln Ala Ile Lys Gln Glu Val Ser Ser Ala
1               5                   10                  15

Leu Gly Ser Pro Gln Phe Met Gln Thr Leu Arg Leu Ala Val Gln Gln
            20                  25                  30

Phe Asp Pro Thr Ala Lys Asp Leu Gln Asp Leu Leu Gln Tyr Leu Cys
        35                  40                  45

Ser Ser Leu Val Val Ser Leu His His Gln Leu Asn Thr Leu Ile
50                  55                  60

Thr Glu Ala Glu Thr Arg Gly Met Thr Gly Tyr Asn Pro Met Ala Gly
65                  70                  75                  80

Pro Leu Arg Met Gln Ala Asn Asn Pro Ala Gln Gln Gly Leu Arg Arg
                85                  90                  95

Glu Tyr Gln Asn Leu Trp Leu Ala Ala Phe Ser Thr Leu Pro Gly Asn
                100                 105                 110

Thr Arg Asp Pro Ser Trp Ala Ala Ile Leu Gln Gly Leu Glu Glu Pro
            115                 120                 125

Tyr Cys Ala Phe Val Glu Arg Leu Asn Val Ala Leu Asp Asn Gly Leu
        130                 135                 140

Pro Glu Gly Thr Pro Lys Glu Pro Ile Leu Arg Ser Leu Ala Tyr Ser
145                 150                 155                 160
```

```
Asn Ala Asn Lys Glu Cys Gln Lys Ile Leu Gln Ala Arg Gly His Thr
                165                 170                 175

Asn Ser Pro Leu Gly Glu Met Leu Arg Thr Cys Gln Ala Trp Thr Pro
            180                 185                 190

Lys Asp Lys Thr Lys Val Leu
        195
```

```
<210> SEQ ID NO 6
<211> LENGTH: 115
<212> TYPE: PRT
<213> ORGANISM: Artificial
<220> FEATURE:
<223> OTHER INFORMATION: similar to human T-cell lymphotropic virus type
      2 but Xaa = Cys or Ala or Ser
<220> FEATURE:
<221> NAME/KEY: MISC_FEATURE
<222> LOCATION: (48)..(48)
<223> OTHER INFORMATION: Xaa = Cys or Ala or Ser

<400> SEQUENCE: 6

Gln Met Lys Asp Leu Gln Ala Ile Lys Gln Glu Val Ser Ser Ser Ala
1               5                   10                  15

Leu Gly Ser Pro Gln Phe Met Gln Thr Leu Arg Leu Ala Val Gln Gln
            20                  25                  30

Phe Asp Pro Thr Ala Lys Asp Leu Gln Asp Leu Leu Gln Tyr Leu Xaa
        35                  40                  45

Ser Ser Leu Val Val Ser Leu His His Gln Gln Leu Asn Thr Leu Ile
    50                  55                  60

Thr Glu Ala Glu Thr Arg Gly Met Thr Gly Tyr Asn Pro Met Ala Gly
65                  70                  75                  80

Pro Leu Arg Met Gln Ala Asn Asn Pro Ala Gln Gln Gly Leu Arg Arg
                85                  90                  95

Glu Tyr Gln Asn Leu Trp Leu Ala Ala Phe Ser Thr Leu Pro Gly Asn
            100                 105                 110

Thr Arg Asp
        115
```

```
<210> SEQ ID NO 7
<211> LENGTH: 84
<212> TYPE: PRT
<213> ORGANISM: Artificial
<220> FEATURE:
<223> OTHER INFORMATION: Similar to Human T-cell lymphotropic virus type
      2 residues 116 to 199, but Xaa = Cys or Ala or Ser
<220> FEATURE:
<221> NAME/KEY: MISC_FEATURE
<222> LOCATION: (15)..(15)
<223> OTHER INFORMATION: Xaa = Cys or Ala or Ser
<220> FEATURE:
<221> NAME/KEY: MISC_FEATURE
<222> LOCATION: (51)..(51)
<223> OTHER INFORMATION: Xaa = Cys or Ala or Ser
<220> FEATURE:
<221> NAME/KEY: MISC_FEATURE
<222> LOCATION: (72)..(72)
<223> OTHER INFORMATION: Xaa = Cys or Ala or Ser

<400> SEQUENCE: 7

Pro Ser Trp Ala Ala Ile Leu Gln Gly Leu Glu Glu Pro Tyr Xaa Ala
1               5                   10                  15

Phe Val Glu Arg Leu Asn Val Ala Leu Asp Asn Gly Leu Pro Glu Gly
            20                  25                  30

Thr Pro Lys Glu Pro Ile Leu Arg Ser Leu Ala Tyr Ser Asn Ala Asn
        35                  40                  45
```

-continued

```
Lys Glu Xaa Gln Lys Ile Leu Gln Ala Arg Gly His Thr Asn Ser Pro
 50                  55                  60
Leu Gly Glu Met Leu Arg Thr Xaa Gln Ala Trp Thr Pro Lys Asp Lys
 65                  70                  75                  80
Thr Lys Val Leu

<210> SEQ ID NO 8
<211> LENGTH: 199
<212> TYPE: PRT
<213> ORGANISM: Artificial
<220> FEATURE:
<223> OTHER INFORMATION: Similar to Human T-cell lymphotropic virus type
      2 residues 116 to 199, but Xaa = Cys or Ala or Ser
<220> FEATURE:
<221> NAME/KEY: MISC_FEATURE
<222> LOCATION: (48)..(48)
<223> OTHER INFORMATION: Xaa = Cys or Ala or Ser
<220> FEATURE:
<221> NAME/KEY: MISC_FEATURE
<222> LOCATION: (130)..(130)
<223> OTHER INFORMATION: Xaa = Cys or Ala or Ser
<220> FEATURE:
<221> NAME/KEY: MISC_FEATURE
<222> LOCATION: (166)..(166)
<223> OTHER INFORMATION: Xaa = Cys or Ala or Ser
<220> FEATURE:
<221> NAME/KEY: MISC_FEATURE
<222> LOCATION: (187)..(187)
<223> OTHER INFORMATION: Xaa = Cys or Ala or Ser

<400> SEQUENCE: 8

Gln Met Lys Asp Leu Gln Ala Ile Lys Gln Glu Val Ser Ser Ser Ala
 1               5                   10                  15
Leu Gly Ser Pro Gln Phe Met Gln Thr Leu Arg Leu Ala Val Gln Gln
                 20                  25                  30
Phe Asp Pro Thr Ala Lys Asp Leu Gln Asp Leu Leu Gln Tyr Leu Xaa
             35                  40                  45
Ser Ser Leu Val Val Ser Leu His His Gln Gln Leu Asn Thr Leu Ile
 50                  55                  60
Thr Glu Ala Glu Thr Arg Gly Met Thr Gly Tyr Asn Pro Met Ala Gly
 65                  70                  75                  80
Pro Leu Arg Met Gln Ala Asn Asn Pro Ala Gln Gln Gly Leu Arg Arg
                 85                  90                  95
Glu Tyr Gln Asn Leu Trp Leu Ala Ala Phe Ser Thr Leu Pro Gly Asn
             100                 105                 110
Thr Arg Asp Pro Ser Trp Ala Ala Ile Leu Gln Gly Leu Glu Glu Pro
         115                 120                 125
Tyr Xaa Ala Phe Val Glu Arg Leu Asn Val Ala Leu Asp Asn Gly Leu
 130                 135                 140
Pro Glu Gly Thr Pro Lys Glu Pro Ile Leu Arg Ser Leu Ala Tyr Ser
145                 150                 155                 160
Asn Ala Asn Lys Glu Xaa Gln Lys Ile Leu Gln Ala Arg Gly His Thr
                 165                 170                 175
Asn Ser Pro Leu Gly Glu Met Leu Arg Thr Xaa Gln Ala Trp Thr Pro
             180                 185                 190
Lys Asp Lys Thr Lys Val Leu
         195

<210> SEQ ID NO 9
<211> LENGTH: 582
<212> TYPE: PRT
```

<213> ORGANISM: Artificial
<220> FEATURE:
<223> OTHER INFORMATION: Fusion protein EcSlyD-EcSlyD-p24(146-344)/HTLV-I.

<400> SEQUENCE: 9

```
Met Lys Val Ala Lys Asp Le

Gln Glu Val Ser Gln Ala Ala Pro Gly Ser Pro Gln Phe Met Gln Thr
385                 390                 395                 400

Ile Arg Leu Ala Val Gln Gln Phe Asp Pro Thr Ala Lys Asp Leu Gln
            405                 410                 415

Asp Leu Leu Gln Tyr Leu Ala Ser Ser Leu Val Ala Ser Leu His His
        420                 425                 430

Gln Gln Leu Asp Ser Leu Ile Ser Glu Ala Glu Thr Arg Gly Ile Thr
    435                 440                 445

Gly Tyr Asn Pro Leu Ala Gly Pro Leu Arg Val Gln Ala Asn Asn Pro
        450                 455                 460

Gln Gln Gln Gly Leu Arg Arg Glu Tyr Gln Gln Leu Trp Leu Ala Ala
465                 470                 475                 480

Phe Ala Ala Leu Pro Gly Ser Ala Lys Asp Pro Ser Trp Ala Ser Ile
            485                 490                 495

Leu Gln Gly Leu Glu Glu Pro Tyr His Ala Phe Val Glu Arg Leu Asn
        500                 505                 510

Ile Ala Leu Asp Asn Gly Leu Pro Glu Gly Thr Pro Lys Asp Pro Ile
    515                 520                 525

Leu Arg Ser Leu Ala Tyr Ser Asn Ala Asn Lys Glu Ala Gln Lys Leu
        530                 535                 540

Leu Gln Ala Arg Gly His Thr Asn Ser Pro Leu Gly Asp Met Leu Arg
545                 550                 555                 560

Ala Ala Gln Thr Trp Thr Pro Lys Asp Lys Thr Lys Val Leu Leu Glu
            565                 570                 575

His His His His His His
            580

<210> SEQ ID NO 10
<211> LENGTH: 476
<212> TYPE: PRT
<213> ORGANISM: Artificial
<220> FEATURE:
<223> OTHER INFORMATION: Fusion protein EcFkpA-p24(146-344)/HTLV-I

<400> SEQUENCE: 10

Met Ala Glu Ala Ala Lys Pro Ala Thr Thr Ala Asp Ser Lys Ala Ala
1 5 10 15

Phe Lys Asn Asp Asp Gln Lys Ser Ala Tyr Ala Leu Gly Ala Ser Leu
20 25 30

Gly Arg Tyr Met Glu Asn Ser Leu Lys Glu Gln Glu Lys Leu Gly Ile
35 40 45

Lys Leu Asp Lys Asp Gln Leu Ile Ala Gly Val Gln Asp Ala Phe Ala
50 55 60

Asp Lys Ser Lys Leu Ser Asp Gln Glu Ile Glu Gln Thr Leu Gln Ala
65 70 75 80

Phe Glu Ala Arg Val Lys Ser Ser Ala Gln Ala Lys Met Glu Lys Asp
85 90 95

Ala Ala Asp Asn Glu Ala Lys Gly Lys Glu Tyr Arg Glu Lys Phe Ala
100 105 110

Lys Glu Lys Gly Val Lys Thr Ser Ser Thr Gly Leu Val Tyr Gln Val
115 120 125

Val Glu Ala Gly Lys Gly Glu Ala Pro Lys Asp Ser Asp Thr Val Val
130 135 140

Val Asn Tyr Lys Gly Thr Leu Ile Asp Gly Lys Glu Phe Asp Asn Ser
145 150 155 160

```
Tyr Thr Arg Gly Glu Pro Leu Ser Phe Arg Leu Asp Gly Val Ile Pro
                165                 170                 175
Gly Trp Thr Glu Gly Leu Lys Asn Ile Lys Lys Gly Lys Ile Lys
        180                 185                 190
Leu Val Ile Pro Pro Glu Leu Ala Tyr Gly Lys Ala Gly Val Pro Gly
            195                 200                 205
Ile Pro Pro Asn Ser Thr Leu Val Phe Asp Val Glu Leu Leu Asp Val
210                 215                 220
Lys Pro Ala Pro Lys Ala Asp Ala Lys Pro Glu Ala Asp Ala Lys Ala
225                 230                 235                 240
Ala Asp Ser Ala Lys Lys Gly Gly Ser Gly Gly Ser Gly Gly
                245                 250                 255
Gly Ser Gly Gly Gly Ser Gly Gly Ser Gly Gly Gly Gln Met Lys
            260                 265                 270
Asp Leu Gln Ala Ile Lys Gln Glu Val Ser Gln Ala Ala Pro Gly Ser
            275                 280                 285
Pro Gln Phe Met Gln Thr Ile Arg Leu Ala Val Gln Gln Phe Asp Pro
        290                 295                 300
Thr Ala Lys Asp Leu Gln Asp Leu Leu Gln Tyr Leu Ala Ser Ser Leu
305                 310                 315                 320
Val Ala Ser Leu His His Gln Leu Asp Ser Leu Ile Ser Glu Ala
                325                 330                 335
Glu Thr Arg Gly Ile Thr Gly Tyr Asn Pro Leu Ala Gly Pro Leu Arg
            340                 345                 350
Val Gln Ala Asn Asn Pro Gln Gln Gln Gly Leu Arg Arg Glu Tyr Gln
            355                 360                 365
Gln Leu Trp Leu Ala Ala Phe Ala Ala Leu Pro Gly Ser Ala Lys Asp
    370                 375                 380
Pro Ser Trp Ala Ser Ile Leu Gln Gly Leu Glu Glu Pro Tyr His Ala
385                 390                 395                 400
Phe Val Glu Arg Leu Asn Ile Ala Leu Asp Asn Gly Leu Pro Glu Gly
                405                 410                 415
Thr Pro Lys Asp Pro Ile Leu Arg Ser Leu Ala Tyr Ser Asn Ala Asn
            420                 425                 430
Lys Glu Ala Gln Lys Leu Leu Gln Ala Arg Gly His Thr Asn Ser Pro
435                 440                 445
Leu Gly Asp Met Leu Arg Ala Ala Gln Thr Trp Thr Pro Lys Asp Lys
            450                 455                 460
Thr Lys Val Leu Leu Glu His His His His His
465                 470                 475

<210> SEQ ID NO 11
<211> LENGTH: 469
<212> TYPE: PRT
<213> ORGANISM: Artificial
<220> FEATURE:
<223> OTHER INFORMATION: Fusion protein EcSlyD-EcSlyD-p24/CTD(258-
      344)/HTLV-I

<400> SEQUENCE: 11

Met Lys Val Ala Lys Asp Leu Val Val Ser Leu Ala Tyr Gln Val Arg
1               5                   10                  15
Thr Glu Asp Gly Val Leu Val Asp Glu Ser Pro Val Ser Ala Pro Leu
            20                  25                  30
Asp Tyr Leu His Gly His Gly Ser Leu Ile Ser Gly Leu Glu Thr Ala
        35                  40                  45
```

```
Leu Glu Gly His Glu Val Gly Asp Lys Phe Asp Val Ala Val Gly Ala
 50                  55                  60

Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                 85                  90                  95

Leu Ala Glu Thr Asp Gln Gly Pro Val Pro Val Glu Ile Thr Ala Val
             100                 105                 110

Glu Asp Asp His Val Val Asp Gly Asn His Met Leu Ala Gly Gln
         115                 120                 125

Asn Leu Lys Phe Asn Val Glu Val Val Ala Ile Arg Glu Ala Thr Glu
130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
             165                 170                 175

Ser Gly Gly Gly Ser Gly Gly Gly Ser Gly Gly Gly Lys Val Ala Lys
             180                 185                 190

Asp Leu Val Val Ser Leu Ala Tyr Gln Val Arg Thr Glu Asp Gly Val
         195                 200                 205

Leu Val Asp Glu Ser Pro Val Ser Ala Pro Leu Asp Tyr Leu His Gly
210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
             245                 250                 255

Gln Tyr Asp Glu Asn Leu Val Gln Arg Val Pro Lys Asp Val Phe Met
         260                 265                 270

Gly Val Asp Glu Leu Gln Val Gly Met Arg Phe Leu Ala Glu Thr Asp
         275                 280                 285

Gln Gly Pro Val Pro Val Glu Ile Thr Ala Val Glu Asp Asp His Val
         290                 295                 300

Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
             325                 330                 335

Gly His Val His Gly Ala His Asp His His Asp His Asp
             340                 345                 350

Gly Gly Gly Ser Gly Gly Gly Ser Gly Gly Gly Ser Gly Gly Gly Ser
             355                 360                 365

Gly Gly Gly Ser Gly Gly Gly Ala Lys Asp Pro Ser Trp Ala Ser Ile
             370                 375                 380

Leu Gln Gly Leu Glu Glu Pro Tyr His Ala Phe Val Glu Arg Leu Asn
385                 390                 395                 400

Ile Ala Leu Asp Asn Gly Leu Pro Glu Gly Thr Pro Lys Asp Pro Ile
                 405                 410                 415

Leu Arg Ser Leu Ala Tyr Ser Asn Ala Asn Lys Glu Ala Gln Lys Leu
             420                 425                 430

Leu Gln Ala Arg Gly His Thr Asn Ser Pro Leu Gly Asp Met Leu Arg
         435                 440                 445

Ala Ala Gln Thr Trp Thr Pro Lys Asp Lys Thr Lys Val Leu Glu His
450                 455                 460
```

His His His His His
465

<210> SEQ ID NO 12
<211> LENGTH: 363
<212> TYPE: PRT
<213> ORGANISM: Artificial
<220> FEATURE:
<223> OTHER INFORMATION: Fusion protein EcFkpA-p24/CTD(258-344)/HTLV-I

<400> SEQUENCE: 12

Met Ala Glu Ala Ala Lys Pro Ala Thr Thr Ala Asp Ser Lys Ala Ala
1               5                   10                  15

Phe Lys Asn Asp Asp Gln Lys Ser Ala Tyr Ala Leu Gly Ala Ser Leu
            20                  25                  30

Gly Arg Tyr Met Glu Asn Ser Leu Lys Glu Gln Glu Lys Leu Gly Ile
        35                  40                  45

Lys Leu Asp Lys Asp Gln Leu Ile Ala Gly Val Gln Asp Ala Phe Ala
    50                  55                  60

Asp Lys Ser Lys Leu Ser Asp Gln Glu Ile Glu Gln Thr Leu Gln Ala
65                  70                  75                  80

Phe Glu Ala Arg Val Lys Ser Ser Ala Gln Ala Lys Met Glu Lys Asp
                85                  90                  95

Ala Ala Asp Asn Glu Ala Lys Gly Lys Glu Tyr Arg Glu Lys Phe Ala
            100                 105                 110

Lys Glu Lys Gly Val Lys Thr Ser Ser Thr Gly Leu Val Tyr Gln Val
        115                 120                 125

Val Glu Ala Gly Lys Gly Glu Ala Pro Lys Asp Ser Asp Thr Val Val
130                 135                 140

Val Asn Tyr Lys Gly Thr Leu Ile Asp Gly Lys Glu Phe Asp Asn Ser
145                 150                 155                 160

Tyr Thr Arg Gly Glu Pro Leu Ser Phe Arg Leu Asp Gly Val Ile Pro
                165                 170                 175

Gly Trp Thr Glu Gly Leu Lys Asn Ile Lys Lys Gly Gly Lys Ile Lys
            180                 185                 190

Leu Val Ile Pro Pro Glu Leu Ala Tyr Gly Lys Ala Gly Val Pro Gly
        195                 200                 205

Ile Pro Pro Asn Ser Thr Leu Val Phe Asp Val Glu Leu Leu Asp Val
    210                 215                 220

Lys Pro Ala Pro Lys Ala Asp Ala Lys Pro Glu Ala Asp Ala Lys Ala
225                 230                 235                 240

Ala Asp Ser Ala Lys Lys Gly Gly Gly Gly Gly Ser Gly Gly Gly Gly
                245                 250                 255

Gly Ser Gly Gly Gly Ser Gly Gly Ser Gly Gly Gly Ala Lys Asp
            260                 265                 270

Pro Ser Trp Ala Ser Ile Leu Gln Gly Leu Glu Glu Pro Tyr His Ala
        275                 280                 285

Phe Val Glu Arg Leu Asn Ile Ala Leu Asp Asn Gly Leu Pro Glu Gly
    290                 295                 300

Thr Pro Lys Asp Pro Ile Leu Arg Ser Leu Ala Tyr Ser Asn Ala Asn
305                 310                 315                 320

Lys Glu Ala Gln Lys Leu Leu Gln Ala Arg Gly His Thr Asn Ser Pro
                325                 330                 335

Leu Gly Asp Met Leu Arg Ala Ala Gln Thr Trp Thr Pro Lys Asp Lys
            340                 345                 350

```
Thr Lys Val Leu Glu His His His His His
        355                 360

<210> SEQ ID NO 13
<211> LENGTH: 259
<212> TYPE: PRT
<213> ORGANISM: Artificial
<220> FEATURE:
<223> OTHER INFORMATION: Fusion protein EcSkp-p24/CTD(258-344)/HTLV-I

<400> SEQUENCE: 13

Met Ala Asp Lys Ile Ala Ile Val Asn Met Gly Ser Leu Phe Gln Gln
1               5                   10                  15

Val Ala Gln Lys Thr Gly Val Ser Asn Thr Leu Glu Asn Glu Phe Arg
            20                  25                  30

Gly Arg Ala Ser Glu Leu Gln Arg Met Glu Thr Asp Leu Gln Ala Lys
        35                  40                  45

Met Lys Lys Leu Gln Ser Met Lys Ala Gly Ser Asp Arg Thr Lys Leu
    50                  55                  60

Glu Lys Asp Val Met Ala Gln Arg Gln Thr Phe Ala Gln Lys Ala Gln
65                  70                  75                  80

Ala Phe Glu Gln Asp Arg Ala Arg Arg Ser Asn Glu Glu Arg Gly Lys
                85                  90                  95

Leu Val Thr Arg Ile Gln Thr Ala Val Lys Ser Val Ala Asn Ser Gln
            100                 105                 110

Asp Ile Asp Leu Val Val Asp Ala Asn Ala Val Ala Tyr Asn Ser Ser
        115                 120                 125

Asp Val Lys Asp Ile Thr Ala Asp Val Leu Lys Gln Val Lys Gly Gly
    130                 135                 140

Gly Ser Gly Gly Gly Ser Gly Gly Gly Ser Gly Gly Gly Ser Gly Gly
145                 150                 155                 160

Gly Ser Gly Gly Gly Ala Lys Asp Pro Ser Trp Ala Ser Ile Leu Gln
                165                 170                 175

Gly Leu Glu Glu Pro Tyr His Ala Phe Val Glu Arg Leu Asn Ile Ala
            180                 185                 190

Leu Asp Asn Gly Leu Pro Glu Gly Thr Pro Lys Asp Pro Ile Leu Arg
        195                 200                 205

Ser Leu Ala Tyr Ser Asn Ala Asn Lys Glu Ala Gln Lys Leu Leu Gln
    210                 215                 220

Ala Arg Gly His Thr Asn Ser Pro Leu Gly Asp Met Leu Arg Ala Ala
225                 230                 235                 240

Gln Thr Trp Thr Pro Lys Asp Lys Thr Lys Val Leu Glu His His His
                245                 250                 255

His His His

<210> SEQ ID NO 14
<211> LENGTH: 498
<212> TYPE: PRT
<213> ORGANISM: Artificial
<220> FEATURE:
<223> OTHER INFORMATION: Fusion protein EcSlyD-EcSlyD-p24/NTD(146-
      260)/HTLV-I

<400> SEQUENCE: 14

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30
```

```
Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
                100                 105                 110

Glu Asp Asp His Val Val Asp Gly Asn His Met Leu Ala Gly Gln
                115                 120                 125

Asn Leu Lys Phe Asn Val Glu Val Val Ala Ile Arg Glu Ala Thr Glu
            130                 135                 140

Glu Glu Leu Ala His Gly His Val His Gly Ala His Asp His His His
145                 150                 155                 160

Asp His Asp His Asp Gly Gly Ser Gly Gly Ser Gly Gly Gly
                165                 170                 175

Ser Gly Gly Gly Ser Gly Gly Ser Gly Gly Gly Lys Val Ala Lys
        180                 185                 190

Asp Leu Val Val Ser Leu Ala Tyr Gln Val Arg Thr Glu Asp Gly Val
            195                 200                 205

Leu Val Asp Glu Ser Pro Val Ser Ala Pro Leu Asp Tyr Leu His Gly
            210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
                260                 265                 270

Gly Val Asp Glu Leu Gln Val Gly Met Arg Phe Leu Ala Glu Thr Asp
            275                 280                 285

Gln Gly Pro Val Pro Val Glu Ile Thr Ala Val Glu Asp Asp His Val
            290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His Asp His Asp His Asp
                340                 345                 350

Gly Gly Gly Ser Gly Gly Gly Ser Gly Gly Gly Ser Gly Gly Gly Ser
            355                 360                 365

Gly Gly Gly Ser Gly Gly Gly Gln Met Lys Asp Leu Gln Ala Ile Lys
        370                 375                 380

Gln Glu Val Ser Gln Ala Ala Pro Gly Ser Pro Gln Phe Met Gln Thr
385                 390                 395                 400

Ile Arg Leu Ala Val Gln Gln Phe Asp Pro Thr Ala Lys Asp Leu Gln
                405                 410                 415

Asp Leu Leu Gln Tyr Leu Ala Ser Ser Leu Val Ala Ser Leu His His
                420                 425                 430

Gln Gln Leu Asp Ser Leu Ile Ser Glu Ala Glu Thr Arg Gly Ile Thr
            435                 440                 445
```

-continued

```
Gly Tyr Asn Pro Leu Ala Gly Pro Leu Arg Val Gln Ala Asn Asn Pro
    450                 455                 460

Gln Gln Gln Gly Leu Arg Arg Glu Tyr Gln Gln Leu Trp Leu Ala Ala
465                 470                 475                 480

Phe Ala Ala Leu Pro Gly Ser Ala Lys Asp Leu Glu His His His His
                485                 490                 495

His His

<210> SEQ ID NO 15
<211> LENGTH: 392
<212> TYPE: PRT
<213> ORGANISM: Artificial
<220> FEATURE:
<223> OTHER INFORMATION: Fusion protein EcFkpA-p24/NTD(146-260)/HTLV-I

<400> SEQUENCE: 15

Met Ala Glu Ala Ala Lys Pro Ala Thr Thr Ala Asp Ser Lys Ala Ala
1               5                   10                  15

Phe Lys Asn Asp Asp Gln Lys Ser Ala Tyr Ala Leu Gly Ala Ser Leu
                20                  25                  30

Gly Arg Tyr Met Glu Asn Ser Leu Lys Glu Gln Glu Lys Leu Gly Ile
            35                  40                  45

Lys Leu Asp Lys Asp Gln Leu Ile Ala Gly Val Gln Asp Ala Phe Ala
50                  55                  60

Asp Lys Ser Lys Leu Ser Asp Gln Glu Ile Glu Gln Thr Leu Gln Ala
65                  70                  75                  80

Phe Glu Ala Arg Val Lys Ser Ser Ala Gln Ala Lys Met Glu Lys Asp
                85                  90                  95

Ala Ala Asp Asn Glu Ala Lys Gly Lys Glu Tyr Arg Glu Lys Phe Ala
            100                 105                 110

Lys Glu Lys Gly Val Lys Thr Ser Ser Thr Gly Leu Val Tyr Gln Val
        115                 120                 125

Val Glu Ala Gly Lys Gly Glu Ala Pro Lys Asp Ser Asp Thr Val Val
    130                 135                 140

Val Asn Tyr Lys Gly Thr Leu Ile Asp Gly Lys Glu Phe Asp Asn Ser
145                 150                 155                 160

Tyr Thr Arg Gly Glu Pro Leu Ser Phe Arg Leu Asp Gly Val Ile Pro
                165                 170                 175

Gly Trp Thr Glu Gly Leu Lys Asn Ile Lys Lys Gly Gly Lys Ile Lys
            180                 185                 190

Leu Val Ile Pro Pro Glu Leu Ala Tyr Gly Lys Ala Gly Val Pro Gly
        195                 200                 205

Ile Pro Pro Asn Ser Thr Leu Val Phe Asp Val Glu Leu Leu Asp Val
    210                 215                 220

Lys Pro Ala Pro Lys Ala Asp Ala Lys Pro Glu Ala Asp Ala Lys Ala
225                 230                 235                 240

Ala Asp Ser Ala Lys Lys Gly Gly Ser Gly Gly Ser Gly Gly Ser Gly
                245                 250                 255

Gly Ser Gly Gly Gly Ser Gly Gly Gly Ser Gly Gly Gln Met Lys
            260                 265                 270

Asp Leu Gln Ala Ile Lys Gln Glu Val Ser Gln Ala Ala Pro Gly Ser
        275                 280                 285

Pro Gln Phe Met Gln Thr Ile Arg Leu Ala Val Gln Gln Phe Asp Pro
    290                 295                 300

Thr Ala Lys Asp Leu Gln Asp Leu Leu Gln Tyr Leu Ala Ser Ser Leu
```

```
                    305                 310                 315                 320
Val Ala Ser Leu His His Gln Gln Leu Asp Ser Leu Ile Ser Glu Ala
                325                 330                 335

Glu Thr Arg Gly Ile Thr Gly Tyr Asn Pro Leu Ala Gly Pro Leu Arg
            340                 345                 350

Val Gln Ala Asn Asn Pro Gln Gln Gly Leu Arg Arg Glu Tyr Gln
                355                 360                 365

Gln Leu Trp Leu Ala Ala Phe Ala Ala Leu Pro Gly Ser Ala Lys Asp
        370                 375                 380

Leu Glu His His His His His His
385                 390

<210> SEQ ID NO 16
<211> LENGTH: 288
<212> TYPE: PRT
<213> ORGANISM: Artificial
<220> FEATURE:
<223> OTHER INFORMATION: Fusion protein EcSkp-p24/NTD(146-260)/HTLV-I

<400> SEQUENCE: 16

Met Ala Asp Lys Ile Ala Ile Val Asn Met Gly Ser Leu Phe Gln Gln
1               5                   10                  15

Val Ala Gln Lys Thr Gly Val Ser Asn Thr Leu Glu Asn Glu Phe Arg
                20                  25                  30

Gly Arg Ala Ser Glu Leu Gln Arg Met Glu Thr Asp Leu Gln Ala Lys
            35                  40                  45

Met Lys Lys Leu Gln Ser Met Lys Ala Gly Ser Asp Arg Thr Lys Leu
        50                  55                  60

Glu Lys Asp Val Met Ala Gln Arg Gln Thr Phe Ala Gln Lys Ala Gln
65                  70                  75                  80

Ala Phe Glu Gln Asp Arg Ala Arg Arg Ser Asn Glu Glu Arg Gly Lys
                85                  90                  95

Leu Val Thr Arg Ile Gln Thr Ala Val Lys Ser Val Ala Asn Ser Gln
            100                 105                 110

Asp Ile Asp Leu Val Val Asp Ala Asn Ala Val Ala Tyr Asn Ser Ser
        115                 120                 125

Asp Val Lys Asp Ile Thr Ala Asp Val Leu Lys Gln Val Lys Gly Gly
    130                 135                 140

Gly Ser Gly Gly Gly Ser Gly Gly Gly Ser Gly Gly Gly Ser Gly Gly
145                 150                 155                 160

Gly Ser Gly Gly Gly Gln Met Lys Asp Leu Gln Ala Ile Lys Gln Glu
                165                 170                 175

Val Ser Gln Ala Ala Pro Gly Ser Pro Gln Phe Met Gln Thr Ile Arg
            180                 185                 190

Leu Ala Val Gln Gln Phe Asp Pro Thr Ala Lys Asp Leu Gln Asp Leu
        195                 200                 205

Leu Gln Tyr Leu Ala Ser Ser Leu Val Ala Ser Leu His His Gln Gln
    210                 215                 220

Leu Asp Ser Leu Ile Ser Glu Ala Glu Thr Arg Gly Ile Thr Gly Tyr
225                 230                 235                 240

Asn Pro Leu Ala Gly Pro Leu Arg Val Gln Ala Asn Asn Pro Gln Gln
                245                 250                 255

Gln Gly Leu Arg Arg Glu Tyr Gln Gln Leu Trp Leu Ala Ala Phe Ala
            260                 265                 270

Ala Leu Pro Gly Ser Ala Lys Asp Leu Glu His His His His His His
```

<210> SEQ ID NO 17
<211> LENGTH: 23
<212> TYPE: PRT
<213> ORGANISM: Artificial
<220> FEATURE:
<223> OTHER INFORMATION: glycine-rich linker useful between fused polypeptides

<400> SEQUENCE: 17

Gly Gly Gly Ser Gly Gly Gly Ser Gly Gly Gly Ser Gly Gly Gly Ser
1               5                   10                  15

Gly Gly Gly Ser Gly Gly Gly
            20

<210> SEQ ID NO 18
<211> LENGTH: 582
<212> TYPE: PRT
<213> ORGANISM: Artificial
<220> FEATURE:
<223> OTHER INFORMATION: Fusion protein EcSlyD-EcSlyD-p24(152-350)/HTLV-II

<400> SEQUENCE: 18

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met

```
              260                 265                 270
Gly Val Asp Glu Leu Gln Val Gly Met Arg Phe Leu Ala Glu Thr Asp
            275                 280                 285

Gln Gly Pro Val Pro Val Glu Ile Thr Ala Val Glu Asp Asp His Val
            290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Leu Ala His
                325                 330                 335

Gly His Val His Gly Ala His Asp His His Asp His Asp
            340                 345                 350

Gly Gly Gly Ser Gly Gly Gly Ser Gly Gly Gly Ser Gly Gly Gly Ser
            355                 360                 365

Gly Gly Gly Ser Gly Gly Gly Gln Met Lys Asp Leu Gln Ala Ile Lys
            370                 375                 380

Gln Glu Val Ser Ser Ala Leu Gly Ser Pro Gln Phe Met Gln Thr
385                 390                 395                 400

Leu Arg Leu Ala Val Gln Gln Phe Asp Pro Thr Ala Lys Asp Leu Gln
                405                 410                 415

Asp Leu Leu Gln Tyr Leu Ala Ser Ser Leu Val Val Ser Leu His His
                420                 425                 430

Gln Gln Leu Asn Thr Leu Ile Thr Glu Ala Glu Thr Arg Gly Met Thr
            435                 440                 445

Gly Tyr Asn Pro Met Ala Gly Pro Leu Arg Met Gln Ala Asn Asn Pro
        450                 455                 460

Ala Gln Gln Gly Leu Arg Arg Glu Tyr Gln Asn Leu Trp Leu Ala Ala
465                 470                 475                 480

Phe Ser Thr Leu Pro Gly Asn Thr Arg Asp Pro Ser Trp Ala Ala Ile
                485                 490                 495

Leu Gln Gly Leu Glu Glu Pro Tyr Ala Ala Phe Val Glu Arg Leu Asn
            500                 505                 510

Val Ala Leu Asp Asn Gly Leu Pro Glu Gly Thr Pro Lys Glu Pro Ile
            515                 520                 525

Leu Arg Ser Leu Ala Tyr Ser Asn Ala Asn Lys Glu Ala Gln Lys Ile
        530                 535                 540

Leu Gln Ala Arg Gly His Thr Asn Ser Pro Leu Gly Glu Met Leu Arg
545                 550                 555                 560

Thr Ala Gln Ala Trp Thr Pro Lys Asp Lys Thr Lys Val Leu Leu Glu
                565                 570                 575

His His His His His His
            580

<210> SEQ ID NO 19
<211> LENGTH: 476
<212> TYPE: PRT
<213> ORGANISM: Artificial
<220> FEATURE:
<223> OTHER INFORMATION: Fusion protein EcFkpA-p24(152-350)/HTLV-II

<400> SEQUENCE: 19

Met Ala Glu Ala Ala Lys Pro Ala Thr Thr Ala Asp Ser Lys Ala Ala
1               5                   10                  15

Phe Lys Asn Asp

```
            35                  40                  45
Lys Leu Asp Lys Asp Gln Leu Ile Ala Gly Val Gln Asp Ala Phe Ala
 50                  55                  60

Asp Lys Ser Lys Leu Ser Asp Gln Glu Ile Glu Gln Thr Leu Gln Ala
 65                  70                  75                  80

Phe Glu Ala Arg Val Lys Ser Ser Ala Gln Ala Lys Met Glu Lys Asp
                 85                  90                  95

Ala Ala Asp Asn Glu Ala Lys Gly Lys Glu Tyr Arg Glu Lys Phe Ala
                100                 105                 110

Lys Glu Lys Gly Val Lys Thr Ser Ser Thr Gly Leu Val Tyr Gln Val
            115                 120                 125

Val Glu Ala Gly Lys Gly Glu Ala Pro Lys Asp Ser Asp Thr Val Val
            130                 135                 140

Val Asn Tyr Lys Gly Thr Leu Ile Asp Gly Lys Glu Phe Asp Asn Ser
145                 150                 155                 160

Tyr Thr Arg Gly Glu Pro Leu Ser Phe Arg Leu Asp Gly Val Ile Pro
                165                 170                 175

Gly Trp Thr Glu Gly Leu Lys Asn Ile Lys Lys Gly Gly Lys Ile Lys
                180                 185                 190

Leu Val Ile Pro Pro Glu Leu Ala Tyr Gly Lys Ala Gly Val Pro Gly
            195                 200                 205

Ile Pro Pro Asn Ser Thr Leu Val Phe Asp Val Glu Leu Leu Asp Val
210                 215                 220

Lys Pro Ala Pro Lys Ala Asp Ala Lys Pro Glu Ala Asp Ala Lys Ala
225                 230                 235                 240

Ala Asp Ser Ala Lys Lys Gly Gly Ser Gly Gly Ser Gly Gly Ser Gly
                245                 250                 255

Gly Ser Gly Gly Gly Ser Gly Gly Ser Gly Gly Gly Gln Met Lys
                260                 265                 270

Asp Leu Gln Ala Ile Lys Gln Glu Val Ser Ser Ser Ala Leu Gly Ser
            275                 280                 285

Pro Gln Phe Met Gln Thr Leu Arg Leu Ala Val Gln Gln Phe Asp Pro
            290                 295                 300

Thr Ala Lys Asp Leu Gln Asp Leu Leu Gln Tyr Leu Ala Ser Ser Leu
305                 310                 315                 320

Val Val Ser Leu His His Gln Gln Leu Asn Thr Leu Ile Thr Glu Ala
                325                 330                 335

Glu Thr Arg Gly Met Thr Gly Tyr Asn Pro Met Ala Gly Pro Leu Arg
                340                 345                 350

Met Gln Ala Asn Asn Pro Ala Gln Gln Gly Leu Arg Arg Glu Tyr Gln
            355                 360                 365

Asn Leu Trp Leu Ala Ala Phe Ser Thr Leu Pro Gly Asn Thr Arg Asp
            370                 375                 380

Pro Ser Trp Ala Ala Ile Leu Gln Gly Leu Glu Glu Pro Tyr Ala Ala
385                 390                 395                 400

Phe Val Glu Arg Leu Asn Val Ala Leu Asp Asn Gly Leu Pro Glu Gly
                405                 410                 415

Thr Pro Lys Glu Pro Ile Leu Arg Ser Leu Ala Tyr Ser Asn Ala Asn
                420                 425                 430

Lys Glu Ala Gln Lys Ile Leu Gln Ala Arg Gly His Thr Asn Ser Pro
            435                 440                 445

Leu Gly Glu Met Leu Arg Thr Ala Gln Ala Trp Thr Pro Lys Asp Lys
            450                 455                 460
```

Thr Lys Val Leu Leu Glu His His His His His His
465                 470                 475

<210> SEQ ID NO 20
<211> LENGTH: 372
<212> TYPE: PRT
<213> ORGANISM: Artificial
<220> FEATURE:
<223> OTHER INFORMATION: Fusion protein EcSkp-p24(152-350)/HTLV-II

<400> SEQUENCE: 20

Met Ala Asp Lys Ile Ala Ile Val Asn Met Gly Ser Leu Phe Gln Gln
1               5                   10                  15

Val Ala Gln Lys Thr Gly Val Ser Asn Thr Leu Glu Asn Glu Phe Arg
            20                  25                  30

Gly Arg Ala Ser Glu Leu Gln Arg Met Glu Thr Asp Leu Gln Ala Lys
        35                  40                  45

Met Lys Lys Leu Gln Ser Met Lys Ala Gly Ser Asp Arg Thr Lys Leu
50                  55                  60

Glu Lys Asp Val Met Ala Gln Arg Gln Thr Phe Ala Gln Lys Ala Gln
65                  70                  75                  80

Ala Phe Glu Gln Asp Arg Ala Arg Arg Ser Asn Glu Glu Arg Gly Lys
                85                  90                  95

Leu Val Thr Arg Ile Gln Thr Ala Val Lys Ser Val Ala Asn Ser Gln
            100                 105                 110

Asp Ile Asp Leu Val Val Asp Ala Asn Ala Val Ala Tyr Asn Ser Ser
        115                 120                 125

Asp Val Lys Asp Ile Thr Ala Asp Val Leu Lys Gln Val Lys Gly Gly
130                 135                 140

Gly Ser Gly Gly Gly Ser Gly Gly Ser Gly Gly Ser Gly Gly
145                 150                 155                 160

Gly Ser Gly Gly Gly Gln Met Lys Asp Leu Gln Ala Ile Lys Gln Glu
                165                 170                 175

Val Ser Ser Ser Ala Leu Gly Ser Pro Gln Phe Met Gln Thr Leu Arg
            180                 185                 190

Leu Ala Val Gln Gln Phe Asp Pro Thr Ala Lys Asp Leu Gln Asp Leu
        195                 200                 205

Leu Gln Tyr Leu Ala Ser Ser Leu Val Val Ser Leu His His Gln Gln
210                 215                 220

Leu Asn Thr Leu Ile Thr Glu Ala Glu Thr Arg Gly Met Thr Gly Tyr
225                 230                 235                 240

Asn Pro Met Ala Gly Pro Leu Arg Met Gln Ala Asn Asn Pro Ala Gln
                245                 250                 255

Gln Gly Leu Arg Arg Glu Tyr Gln Asn Leu Trp Leu Ala Ala Phe Ser
            260                 265                 270

Thr Leu Pro Gly Asn Thr Arg Asp Pro Ser Trp Ala Ala Ile Leu Gln
        275                 280                 285

Gly Leu Glu Glu Pro Tyr Ala Ala Phe Val Glu Arg Leu Asn Val Ala
290                 295                 300

Leu Asp Asn Gly Leu Pro Glu Gly Thr Pro Lys Glu Pro Ile Leu Arg
305                 310                 315                 320

Ser Leu Ala Tyr Ser Asn Ala Asn Lys Glu Ala Gln Lys Ile Leu Gln
                325                 330                 335

Ala Arg Gly His Thr Asn Ser Pro Leu Gly Glu Met Leu Arg Thr Ala
            340                 345                 350

Gln Ala Trp Thr Pro Lys Asp Lys Thr Lys Val Leu Leu Glu His His
        355                 360                 365

His His His His
    370

<210> SEQ ID NO 21
<211> LENGTH: 361
<212> TYPE: PRT
<213> ORGANISM: Artificial
<220> FEATURE:
<223> OTHER INFORMATION: Fusion protein EcFkpA-p24/CTD(267-350)/HTLV-II

<400> SEQUENCE: 21

Met Ala Glu Ala Ala Lys Pro Ala Thr Thr Ala Asp Ser Lys Ala Ala
1               5                   10                  15

Phe Lys Asn Asp Asp Gln Lys Ser Ala Tyr Ala Leu Gly Ala Ser Leu
            20                  25                  30

Gly Arg Tyr Met Glu Asn Ser Leu Lys Glu Gln Glu Lys Leu Gly Ile
        35                  40                  45

Lys Leu Asp Lys Asp Gln Leu Ile Ala Gly Val Gln Asp Ala Phe Ala
    50                  55                  60

Asp Lys Ser Lys Leu Ser Asp Gln Glu Ile Glu Gln Thr Leu Gln Ala
65                  70                  75                  80

Phe Glu Ala Arg Val Lys Ser Ser Ala Gln Ala Lys Met Glu Lys Asp
                85                  90                  95

Ala Ala Asp Asn Glu Ala Lys Gly Lys Glu Tyr Arg Glu Lys Phe Ala
            100                 105                 110

Lys Glu Lys Gly Val Lys Thr Ser Ser Thr Gly Leu Val Tyr Gln Val
        115                 120                 125

Val Glu Ala Gly Lys Gly Glu Ala Pro Lys Asp Ser Asp Thr Val Val
    130                 135                 140

Val Asn Tyr Lys Gly Thr Leu Ile Asp Gly Lys Glu Phe Asp Asn Ser
145                 150                 155                 160

Tyr Thr Arg Gly Glu Pro Leu Ser Phe Arg Leu Asp Gly Val Ile Pro
                165                 170                 175

Gly Trp Thr Glu Gly Leu Lys Asn Ile Lys Lys Gly Gly Lys Ile Lys
            180                 185                 190

Leu Val Ile Pro Pro Glu Leu Ala Tyr Gly Lys Ala Gly Val Pro Gly
        195                 200                 205

Ile Pro Pro Asn Ser Thr Leu Val Phe Asp Val Glu Leu Leu Asp Val
    210                 215                 220

Lys Pro Ala Pro Lys Ala Asp Ala Lys Pro Glu Ala Asp Ala Lys Ala
225                 230                 235                 240

Ala Asp Ser Ala Lys Lys Gly Gly Ser Gly Gly Gly Ser Gly Gly Gly
                245                 250                 255

Gly Ser Gly Gly Gly Ser Gly Gly Gly Ser Gly Gly Gly Pro Ser Trp
            260                 265                 270

Ala Ala Ile Leu Gln Gly Leu Glu Glu Pro Tyr Ala Ala Phe Val Glu
        275                 280                 285

Arg Leu Asn Val Ala Leu Asp Asn Gly Leu Pro Glu Gly Thr Pro Lys
    290                 295                 300

Glu Pro Ile Leu Arg Ser Leu Ala Tyr Ser Asn Ala Asn Lys Glu Ala
305                 310                 315                 320

Gln Lys Ile Leu Gln Ala Arg Gly His Thr Asn Ser Pro Leu Gly Glu
                325                 330                 335

Met Leu Arg Thr Ala Gln Ala Trp Thr Pro Lys Asp Lys Thr Lys Val
                340                 345                 350

Leu Leu Glu His His His His His His
        355                 360

<210> SEQ ID NO 22
<211> LENGTH: 257
<212> TYPE: PRT
<213> ORGANISM: Artificial
<220> FEATURE:
<223> OTHER INFORMATION: Fusion protein EcSkp-p24/CTD(267-350)/HTLV-II

<400> SEQUENCE: 22

Met Ala Asp Lys Ile Ala Ile Val Asn Met Gly Ser Leu Phe Gln Gln
1               5                   10                  15

Val Ala Gln Lys Thr Gly Val Ser Asn Thr Leu Glu Asn Glu Phe Arg
            20                  25                  30

Gly Arg Ala Ser Glu Leu Gln Arg Met Glu Thr Asp Leu Gln Ala Lys
        35                  40                  45

Met Lys Lys Leu Gln Ser Met Lys Ala Gly Ser Asp Arg Thr Lys Leu
    50                  55                  60

Glu Lys Asp Val Met Ala Gln Arg Gln Thr Phe Ala Gln Lys Ala Gln
65                  70                  75                  80

Ala Phe Glu Gln Asp Arg Ala Arg Arg Ser Asn Glu Glu Arg Gly Lys
                85                  90                  95

Leu Val Thr Arg Ile Gln Thr Ala Val Lys Ser Val Ala Asn Ser Gln
            100                 105                 110

Asp Ile Asp Leu Val Val Asp Ala Asn Ala Val Ala Tyr Asn Ser Ser
        115                 120                 125

Asp Val Lys Asp Ile Thr Ala Asp Val Leu Lys Gln Val Lys Gly Gly
    130                 135                 140

Gly Ser Gly Gly Gly Ser Gly Gly Gly Ser Gly Gly Gly Ser Gly Gly
145                 150                 155                 160

Gly Ser Gly Gly Gly Pro Ser Trp Ala Ala Ile Leu Gln Gly Leu Glu
                165                 170                 175

Glu Pro Tyr Ala Ala Phe Val Glu Arg Leu Asn Val Ala Leu Asp Asn
            180                 185                 190

Gly Leu Pro Glu Gly Thr Pro Lys Glu Pro Ile Leu Arg Ser Leu Ala
        195                 200                 205

Tyr Ser Asn Ala Asn Lys Glu Ala Gln Lys Ile Leu Gln Ala Arg Gly
    210                 215                 220

His Thr Asn Ser Pro Leu Gly Glu Met Leu Arg Thr Ala Gln Ala Trp
225                 230                 235                 240

Thr Pro Lys Asp Lys Thr Lys Val Leu Leu Glu His His His His
                245                 250                 255

His

<210> SEQ ID NO 23
<211> LENGTH: 392
<212> TYPE: PRT
<213> ORGANISM: Artificial
<220> FEATURE:
<223> OTHER INFORMATION: Fusion protein  EcFkpA-p24/NTD(152-266)/HTLV-II

<400> SEQUENCE: 23

Met Ala Glu Ala Ala Lys Pro Ala Thr Thr Ala Asp Ser Lys Ala Ala
1               5                   10                  15

-continued

Phe Lys Asn Asp Asp Gln Lys Ser Ala Tyr Ala Leu Gly Ala Ser Leu
            20                  25                  30

Gly Arg Tyr Met Glu Asn Ser Leu Lys Glu Gln Glu Lys Leu Gly Ile
        35                  40                  45

Lys Leu Asp Lys Asp Gln Leu Ile Ala Gly Val Gln Asp Ala Phe Ala
50                  55                  60

Asp Lys Ser Lys Leu Ser Asp Gln Glu Ile Glu Gln Thr Leu Gln Ala
65                  70                  75                  80

Phe Glu Ala Arg Val Lys Ser Ser Ala Gln Ala Lys Met Glu Lys Asp
                85                  90                  95

Ala Ala Asp Asn Glu Ala Lys Gly Lys Glu Tyr Arg Glu Lys Phe Ala
            100                 105                 110

Lys Glu Lys Gly Val Lys Thr Ser Ser Thr Gly Leu Val Tyr Gln Val
        115                 120                 125

Val Glu Ala Gly Lys Gly Glu Ala Pro Lys Asp Ser Asp Thr Val Val
130                 135                 140

Val Asn Tyr Lys Gly Thr Leu Ile Asp Gly Lys Glu Phe Asp Asn Ser
145                 150                 155                 160

Tyr Thr Arg Gly Glu Pro Leu Ser Phe Arg Leu Asp Gly Val Ile Pro
                165                 170                 175

Gly Trp Thr Glu Gly Leu Lys Asn Ile Lys Lys Gly Gly Lys Ile Lys
            180                 185                 190

Leu Val Ile Pro Pro Glu Leu Ala Tyr Gly Lys Ala Gly Val Pro Gly
        195                 200                 205

Ile Pro Pro Asn Ser Thr Leu Val Phe Asp Val Glu Leu Leu Asp Val
210                 215                 220

Lys Pro Ala Pro Lys Ala Asp Ala Lys Pro Glu Ala Asp Ala Lys Ala
225                 230                 235                 240

Ala Asp Ser Ala Lys Lys Gly Gly Ser Gly Gly Ser Gly Gly
                245                 250                 255

Gly Ser Gly Gly Gly Ser Gly Gly Ser Gly Gly Gly Gln Met Lys
            260                 265                 270

Asp Leu Gln Ala Ile Lys Gln Glu Val Ser Ser Ser Ala Leu Gly Ser
        275                 280                 285

Pro Gln Phe Met Gln Thr Leu Arg Leu Ala Val Gln Gln Phe Asp Pro
290                 295                 300

Thr Ala Lys Asp Leu Gln Asp Leu Leu Gln Tyr Leu Ala Ser Ser Leu
305                 310                 315                 320

Val Val Ser Leu His His Gln Gln Leu Asn Thr Leu Ile Thr Glu Ala
                325                 330                 335

Glu Thr Arg Gly Met Thr Gly Tyr Asn Pro Met Ala Gly Pro Leu Arg
            340                 345                 350

Met Gln Ala Asn Asn Pro Ala Gln Gln Gly Leu Arg Arg Glu Tyr Gln
        355                 360                 365

Asn Leu Trp Leu Ala Ala Phe Ser Thr Leu Pro Gly Asn Thr Arg Asp
370                 375                 380

Leu Glu His His His His His His
385                 390

<210> SEQ ID NO 24
<211> LENGTH: 288
<212> TYPE: PRT
<213> ORGANISM: Artificial
<220> FEATURE:

<223> OTHER INFORMATION: Fusion protein EcSkp-p24/NTD(152-266)/HTLV-II

<400> SEQUENCE: 24

Met Ala Asp Lys Ile Ala Ile Val Asn Met Gly Ser Leu Phe Gln Gln
1               5                   10                  15

Val Ala Gln Lys Thr Gly Val Ser Asn Thr Leu Glu Asn Glu Phe Arg
20 25 30

Gly Arg Ala Ser Glu Leu Gln Arg Met Glu Thr Asp Leu Gln Ala Lys
35 40 45

Met Lys Lys Leu Gln Ser Met Lys Ala Gly Ser Asp Arg Thr Lys Leu
50 55 60

Glu Lys Asp Val Met Ala Gln Arg Gln Thr Phe Ala Gln Lys Ala Gln
65 70 75 80

Ala Phe Glu Gln Asp Arg Ala Arg Arg Ser Asn Glu Glu Arg Gly Lys
85 90 95

Leu Val Thr Arg Ile Gln Thr Ala Val Lys Ser Val Ala Asn Ser Gln
100 105 110

Asp Ile Asp Leu Val Val Asp Ala Asn Ala Val Ala Tyr Asn Ser Ser
115 120 125

Asp Val Lys Asp Ile Thr Ala Asp Val Leu Lys Gln Val Lys Gly Gly
130 135 140

Gly Ser Gly Gly Gly Ser Gly Gly Gly Ser Gly Gly Gly Ser Gly Gly
145 150 155 160

Gly Ser Gly Gly Gly Gln Met Lys Asp Leu Gln Ala Ile Lys Gln Glu
165 170 175

Val Ser Ser Ser Ala Leu Gly Ser Pro Gln Phe Met Gln Thr Leu Arg
180 185 190

Leu Ala Val Gln Gln Phe Asp Pro Thr Ala Lys Asp Leu Gln Asp Leu
195 200 205

Leu Gln Tyr Leu Ala Ser Ser Leu Val Val Ser Leu His His Gln Gln
210 215 220

Leu Asn Thr Leu Ile Thr Glu Ala Glu Thr Arg Gly Met Thr Gly Tyr
225 230 235 240

Asn Pro Met Ala Gly Pro Leu Arg Met Gln Ala Asn Asn Pro Ala Gln
245 250 255

Gln Gly Leu Arg Arg Glu Tyr Gln Asn Leu Trp Leu Ala Ala Phe Ser
260 265 270

Thr Leu Pro Gly Asn Thr Arg Asp Leu Glu His His His His His His
275 280 285

<210> SEQ ID NO 25
<211> LENGTH: 108
<212> TYPE: PRT
<213> ORGANISM: Artificial
<220> FEATURE:
<223> OTHER INFORMATION: soluble HTLV p24 antigen and an HTLV env
antigen gp21 wherein Xaa= Cys or Ala or Ser
<220> FEATURE:
<221> NAME/KEY: MISC_FEATURE
<222> LOCATION: (55)..(55)
<223> OTHER INFORMATION: Xaa = Cys or Ala or Ser
<220> FEATURE:
<221> NAME/KEY: MISC_FEATURE
<222> LOCATION: (62)..(63)
<223> OTHER INFORMATION: Xaa = Cys or Ala or Ser

<400> SEQUENCE: 25

Ser Leu Ala Ser Gly Lys Ser Leu Leu His Glu Val Asp Lys Asp Ile
1 5 10 15

Ser Gln Leu Thr Gln Ala Ile Val Lys Asn His Lys Asn Leu Leu Lys
          20                  25                  30

Ile Ala Gln Tyr Ala Ala Gln Asn Arg Arg Gly Leu Asp Leu Leu Phe
              35                  40                  45

Trp Glu Gln Gly Gly Leu Xaa Lys Ala Leu Gln Glu Gln Xaa Xaa Phe
50                      55                  60

Leu Asn Ile Thr Asn Ser His Val Ser Ile Leu Gln Glu Arg Pro Pro
65                      70                  75                  80

Leu Glu Asn Arg Val Leu Thr Gly Trp Gly Leu Asn Trp Asp Leu Gly
                  85                  90                  95

Leu Ser Gln Trp Ala Arg Glu Ala Leu Gln Thr Gly
                100                 105

<210> SEQ ID NO 26
<211> LENGTH: 304
<212> TYPE: PRT
<213> ORGANISM: Artificial
<220> FEATURE:
<223> OTHER INFORMATION: Fusion protein EcSlyD-gp21(339-446)/HTLV-1

<400> SEQUENCE: 26

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
              20                  25                  30

Asp Tyr Leu His Gly His Gly Ser Leu Ile Ser Gly Leu Glu Thr Ala
          35                  40                  45

Leu Glu Gly His Glu Val Gly Asp Lys Phe Asp Val Ala Val Gly Ala
50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
              100                 105                 110

Glu Asp Asp His Val Val Asp Gly Asn His Met Leu Ala Gly Gln
          115                 120                 125

Asn Leu Lys Phe Asn Val Glu Val Val Ala Ile Arg Glu Ala Thr Glu
          130                 135                 140

Glu Glu Leu Ala His Gly His Val Gly Ala His Asp His His
145                 150                 155                 160

Asp His Asp His Asp Gly Gly Ser Gly Gly Gly Ser Gly Gly Gly
              165                 170                 175

Ser Gly Gly Gly Ser Gly Gly Gly Ser Gly Gly Gly Ser Leu Ala Ser
              180                 185                 190

Gly Lys Ser Leu Leu His Glu Val Asp Lys Asp Ile Ser Gln Leu Thr
          195                 200                 205

Gln Ala Ile Val Lys Asn His Lys Asn Leu Leu Lys Ile Ala Gln Tyr
          210                 215                 220

Ala Ala Gln Asn Arg Arg Gly Leu Asp Leu Leu Phe Trp Glu Gln Gly
225                 230                 235                 240

Gly Leu Ala Lys Ala Leu Gln Glu Gln Ala Ala Phe Leu Asn Ile Thr
              245                 250                 255

Asn Ser His Val Ser Ile Leu Gln Glu Arg Pro Pro Leu Glu Asn Arg
          260                 265                 270

-continued

```
Val Leu Thr Gly Trp Gly Leu Asn Trp Asp Leu Gly Leu Ser Gln Trp
        275                 280                 285

Ala Arg Glu Ala Leu Gln Thr Gly Leu Glu His His His His His His
    290                 295                 300

<210> SEQ ID NO 27
<211> LENGTH: 286
<212> TYPE: PRT
<213> ORGANISM: Artificial
<220> FEATURE:
<223> OTHER INFORMATION: Fusion protein EcSlpA-gp21(339-446)/HTLV-1

<400> SEQUENCE: 27

Ser Glu Ser Val Gln Ser Asn Ser Ala Val Leu Val His Phe Thr Leu
1               5                   10                  15

Lys Leu Asp Asp Gly Thr Thr Ala Glu Ser Thr Arg Asn Asn Gly Lys
            20                  25                  30

Pro Ala Leu Phe Arg Leu Gly Asp Ala Ser Leu Ser Glu Gly Leu Glu
        35                  40                  45

Gln His Leu Leu Gly Leu Lys Val Gly Asp Lys Thr Thr Phe Ser Leu
    50                  55                  60

Glu Pro Asp Ala Ala Phe Gly Val Pro Ser Pro Asp Leu Ile Gln Tyr
65                  70                  75                  80

Phe Ser Arg Arg Glu Phe Met Asp Ala Gly Glu Pro Glu Ile Gly Ala
                85                  90                  95

Ile Met Leu Phe Thr Ala Met Asp Gly Ser Glu Met Pro Gly Val Ile
            100                 105                 110

Arg Glu Ile Asn Gly Asp Ser Ile Thr Val Asp Phe Asn His Pro Leu
        115                 120                 125

Ala Gly Gln Thr Val His Phe Asp Ile Glu Val Leu Glu Ile Asp Pro
    130                 135                 140

Ala Leu Glu Gly Gly Gly Ser Gly Gly Gly Ser Gly Gly Gly Ser Gly
145                 150                 155                 160

Gly Gly Ser Gly Gly Gly Ser Gly Gly Gly Ser Leu Ala Ser Gly Lys
                165                 170                 175

Ser Leu Leu His Glu Val Asp Lys Asp Ile Ser Gln Leu Thr Gln Ala
            180                 185                 190

Ile Val Lys Asn His Lys Asn Leu Leu Lys Ile Ala Gln Tyr Ala Ala
        195                 200                 205

Gln Asn Arg Arg Gly Leu Asp Leu Leu Phe Trp Glu Gln Gly Gly Leu
    210                 215                 220

Ala Lys Ala Leu Gln Glu Gln Ala Ala Phe Leu Asn Ile Thr Asn Ser
225                 230                 235                 240

His Val Ser Ile Leu Gln Glu Arg Pro Pro Leu Glu Asn Arg Val Leu
                245                 250                 255

Thr Gly Trp Gly Leu Asn Trp Asp Leu Gly Leu Ser Gln Trp Ala Arg
            260                 265                 270

Glu Ala Leu Gln Thr Gly Leu Glu His His His His His His
        275                 280                 285
```